(12) United States Patent
Kim et al.

(10) Patent No.: US 11,389,508 B2
(45) Date of Patent: Jul. 19, 2022

(54) PROTEIN COMPLEX BY USE OF A SPECIFIC SITE OF AN IMMUNOGLOBULIN FRAGMENT FOR LINKAGE

(71) Applicant: HANMI PHARM. CO., LTD, Hwaseong-si (KR)

(72) Inventors: Dae Jin Kim, Hwaseong-si (KR); Jong Soo Lee, Hwaseong-si (KR); Young Jin Park, Hwaseong-si (KR); Sung Hee Hong, Hwaseong-si (KR); Sung Min Bae, Hwaseong-si (KR); Se Chang Kwon, Hwaseong-si (KR)

(73) Assignee: HANMI PHARM. CO., LTD., Hwaseong-si (KR)

(*) Notice: Subject to any disclaimer, the term of this patent is extended or adjusted under 35 U.S.C. 154(b) by 0 days.

(21) Appl. No.: 15/762,661

(22) PCT Filed: Sep. 26, 2016

(86) PCT No.: PCT/KR2016/010762
§ 371 (c)(1),
(2) Date: Mar. 23, 2018

(87) PCT Pub. No.: WO2017/052329
PCT Pub. Date: Mar. 30, 2017

(65) Prior Publication Data
US 2018/0326013 A1 Nov. 15, 2018

(30) Foreign Application Priority Data
Sep. 24, 2015 (KR) .................. 10-2015-0135874

(51) Int. Cl.
| | | |
|---|---|---|
| *A61K 38/21* | (2006.01) | |
| *A61K 47/68* | (2017.01) | |
| *C07K 14/535* | (2006.01) | |
| *A61K 47/60* | (2017.01) | |
| *B01D 15/36* | (2006.01) | |
| *B01D 15/38* | (2006.01) | |
| *B01D 15/32* | (2006.01) | |
| *B01D 15/34* | (2006.01) | |
| *A61K 38/19* | (2006.01) | |

(52) U.S. Cl.
CPC ............ *A61K 38/212* (2013.01); *A61K 47/60* (2017.08); *A61K 47/68* (2017.08); *C07K 14/535* (2013.01); *A61K 38/195* (2013.01); *A61K 47/6813* (2017.08); *B01D 15/327* (2013.01); *B01D 15/34* (2013.01); *B01D 15/362* (2013.01); *B01D 15/363* (2013.01); *B01D 15/3804* (2013.01); *C07K 2317/52* (2013.01); *C07K 2317/522* (2013.01); *C07K 2317/524* (2013.01); *C07K 2317/526* (2013.01); *C07K 2317/528* (2013.01)

(58) Field of Classification Search
CPC ...... A61K 38/212; A61K 47/60; A61K 47/68; A61K 38/195; A61K 47/6813; A61K 47/6801; C07K 14/535; C07K 2317/52; C07K 2317/522; C07K 2317/524; C07K 2317/526; C07K 2317/528; C07K 1/18; C07K 1/22; C07K 1/36; B01D 15/327; B01D 15/34; B01D 15/362; B01D 15/363; B01D 15/3804; B01D 15/305; A61P 5/00; A61P 5/06; A61P 5/14; A61P 5/18; A61P 5/48; A61P 5/50; A61P 7/04; A61P 37/04; A61P 43/00
See application file for complete search history.

(56) References Cited

U.S. PATENT DOCUMENTS

| | | | | |
|---|---|---|---|---|
| 5,773,581 A | * | 6/1998 | Camble | ................... A61P 31/12 530/351 |
| 2006/0269553 A1 | * | 11/2006 | Kim | ....................... C07K 19/00 424/155.1 |
| 2009/0053246 A1 | | 2/2009 | Kim et al. | |
| 2010/0105877 A1 | * | 4/2010 | Song | ......................... A61P 3/08 530/391.9 |
| 2010/0261248 A1 | | 10/2010 | Kim et al. | |

(Continued)

FOREIGN PATENT DOCUMENTS

| | | |
|---|---|---|
| CN | 1723219 B | 5/2010 |
| CN | 103212084 A | 7/2013 |

(Continued)

OTHER PUBLICATIONS

Burgess et al., Journal of Cell Biology 111:2129-2138 (Year: 1990).*

(Continued)

*Primary Examiner* — Phuong Huynh
(74) *Attorney, Agent, or Firm* — Sughrue Mion, PLLC

(57) ABSTRACT

Provided is a complex composition, of which positional isomers are minimized by using a N-terminus of an immunoglobulin Fc region as a binding site when the immunoglobulin Fc region is used as a carrier. Also provided are a protein complex which is prepared by N-terminal-specific binding of immunoglobulin Fc region, thereby prolonging blood half-life of the physiologically active polypeptide, maintaining in vivo potency at a high level, and having no risk of immune responses, a preparation method thereof, and a pharmaceutical composition including the same for improving in vivo duration and stability of the physiologically active polypeptide. The protein complex prepared by the present invention may be usefully applied to the development of long-acting formulations of various physiologically active polypeptide drugs.

20 Claims, 15 Drawing Sheets
Specification includes a Sequence Listing.

(56) References Cited

U.S. PATENT DOCUMENTS

2013/0122023 A1* 5/2013 Woo .................. A61K 31/4164
424/178.1
2014/0219961 A1 8/2014 Jung et al.

FOREIGN PATENT DOCUMENTS

| JP | 2007-536211 A | 12/2007 | | |
|---|---|---|---|---|
| JP | 2010-515677 A | 5/2010 | | |
| JP | 2015-510880 A | 4/2015 | | |
| KR | 10-2012-0111537 A | 10/2012 | | |
| KR | 10-2013-0103190 A | 9/2013 | | |
| WO | 96/32478 A1 | 10/1996 | | |
| WO | 97/34631 A1 | 9/1997 | | |
| WO | WO-2005047336 A1 * | 5/2005 | ............. | C07K 19/00 |
| WO | WO-2007021129 A1 * | 2/2007 | ............. | C07K 16/00 |
| WO | WO-2010011096 A2 * | 1/2010 | ......... | A61K 47/6889 |
| WO | 2012/011752 A2 | 1/2012 | | |
| WO | 2013/036032 A1 | 3/2013 | | |
| WO | WO-2013100702 A1 * | 7/2013 | ........... | C07K 16/283 |
| WO | 2013/133667 A1 | 9/2013 | | |
| WO | WO-2013133659 A1 * | 9/2013 | ......... | A61K 47/6883 |

OTHER PUBLICATIONS

Lazar et al., Molecular Cellular Biology 8:1247-1252 (Year: 1988).*
European Patent Office, Communication dated Apr. 3, 2019, issued in corresponding European Application No. 16849054.8.
International Search Report for PCT/KR2016/010762, dated Dec. 8, 2016.
Written Opinion of the International Searching Authority for PCT/KR2016/010762, dated Dec. 8, 2016.
Recke et al., "Pathogenicity of IgG subclass autoantibodies to type VII collagen: Induction of dermal-epidermal separation", Journal of Autoimmunity 34(4), 2010, pp. 435-444.
GenBank Database, Accession No. GenBank: ACN59877.1: SEQ ID No. 1 Chimeric Anti-human type VIII collagen Immunoglobulin G4 [Synthetic construct].

* cited by examiner

[Figure 1a]
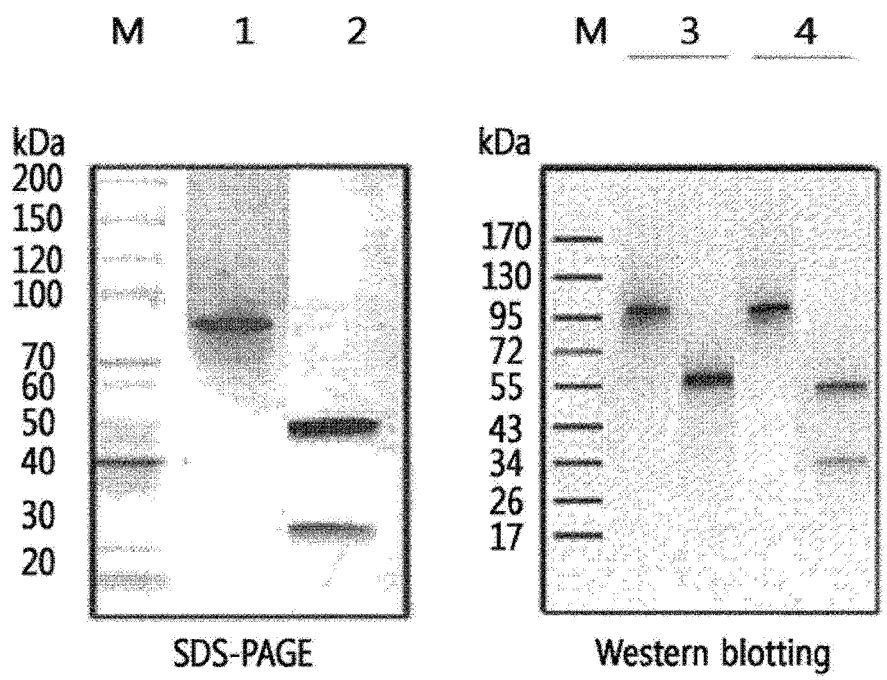
M. Size Marker
1. IFN α-PEG-Fc non-reducing conditions
2. IFN α-PEG-Fc reducing conditions
3. Use of anti-IFN α antibody ( IFN α-PEG-Fc non-reducing, reducing conditions)
4. Use of anti-Fc antibody ( IFN α-PEG-Fc non-reducing, reducing conditions)

[Figure 1b]
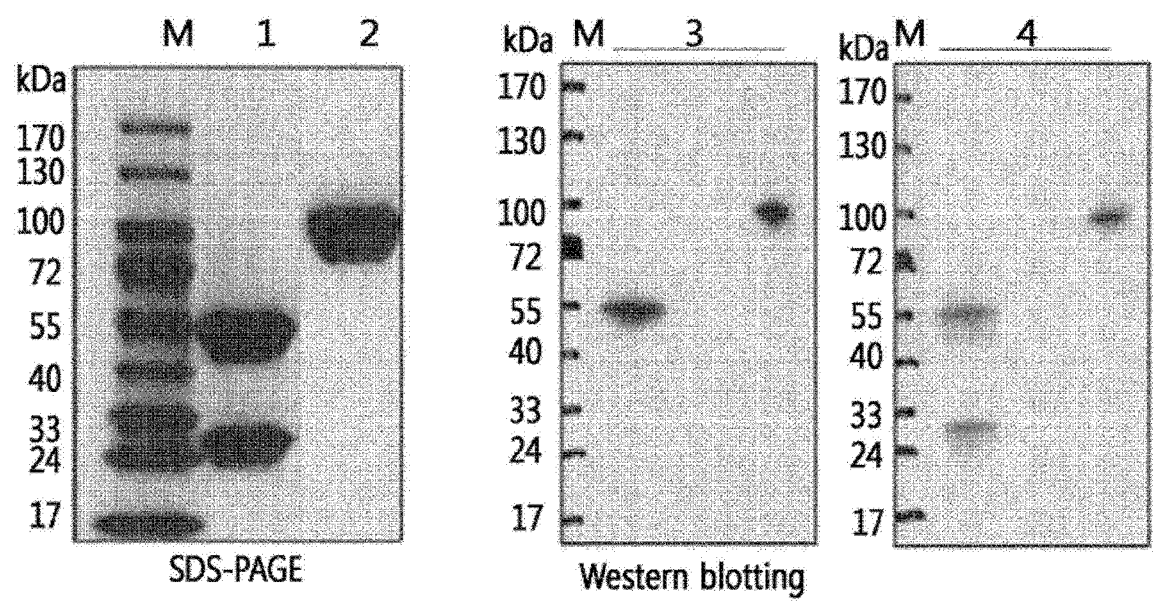
M. Size Marker
1. hGH-PEG-Fc reducing conditions
2. hGH-PEG-Fc non-reducing conditions
3. Use of anti-hGH antibody ( hGH-PEG-Fc reducing, non-reducing conditions)
4. Use of anti-Fc antibody ( hGH-PEG-Fc reducing, non-reducing conditions)

[Figure 1c]
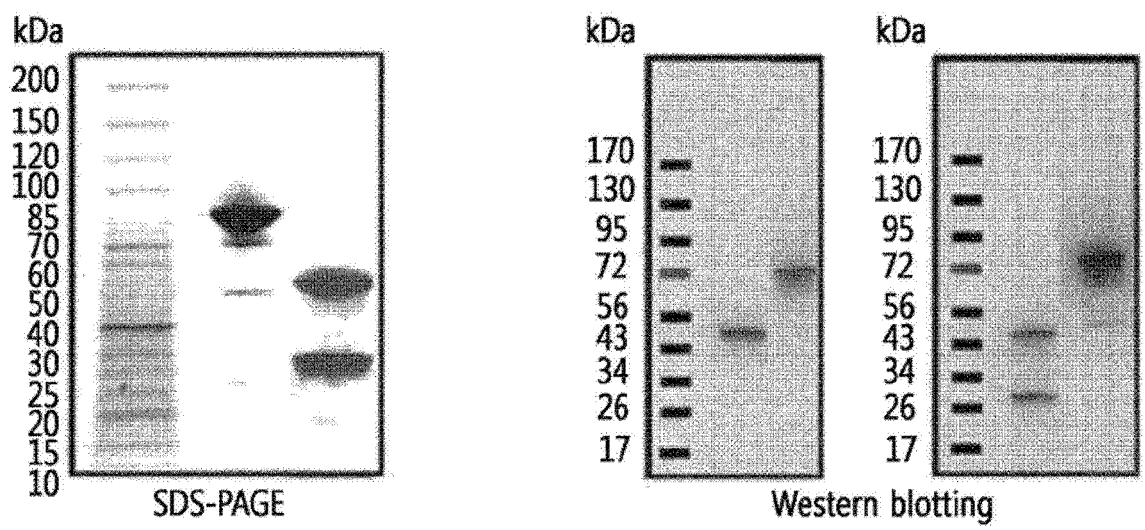
M. Size Marker
1. $^{17.65}$Ser-G-CSF-PEG-Fc non-reducing conditions
2. $^{17.65}$Ser-G-CSF-PEG-Fc reducing conditions
3. Use of anti-G-CSF antibody
( $^{17.65}$Ser-G-CSF-PEG-Fc reducing, non-reducing conditions)
4. Use of anti-Fc antibody
( $^{17.65}$Ser-G-CSF-PEG-Fc reducing, non-reducing conditions)

[Figure 1d]
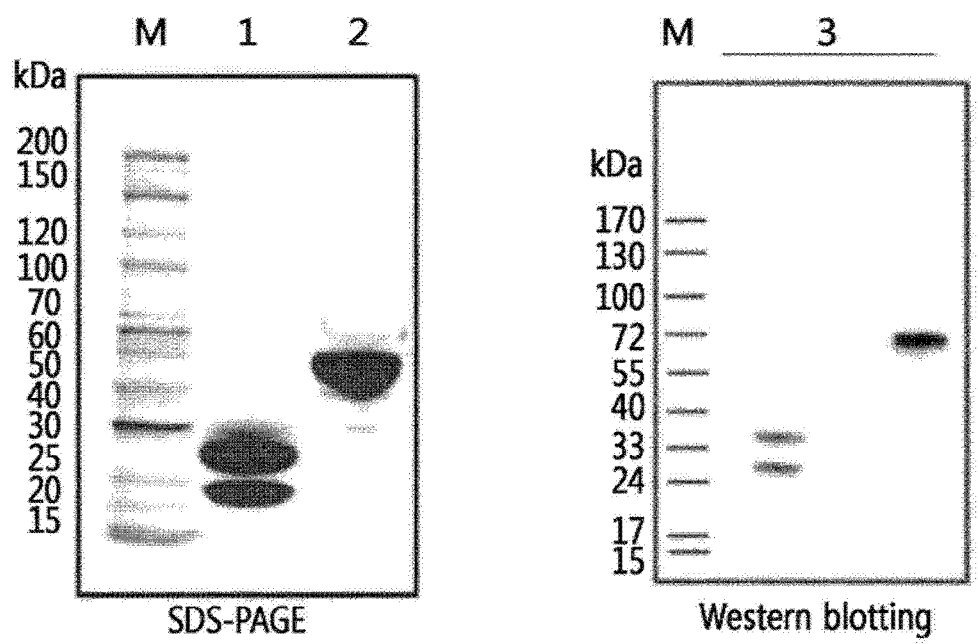
M. Size Marker
1. Insulin-PEG-Fc reducing conditions
2. Insulin-PEG-Fc non-reducing conditions
3. Use of anti-Fc antibody
(Insulin-PEG-Fc reducing, non-reducing conditions)

[Figure 1e]
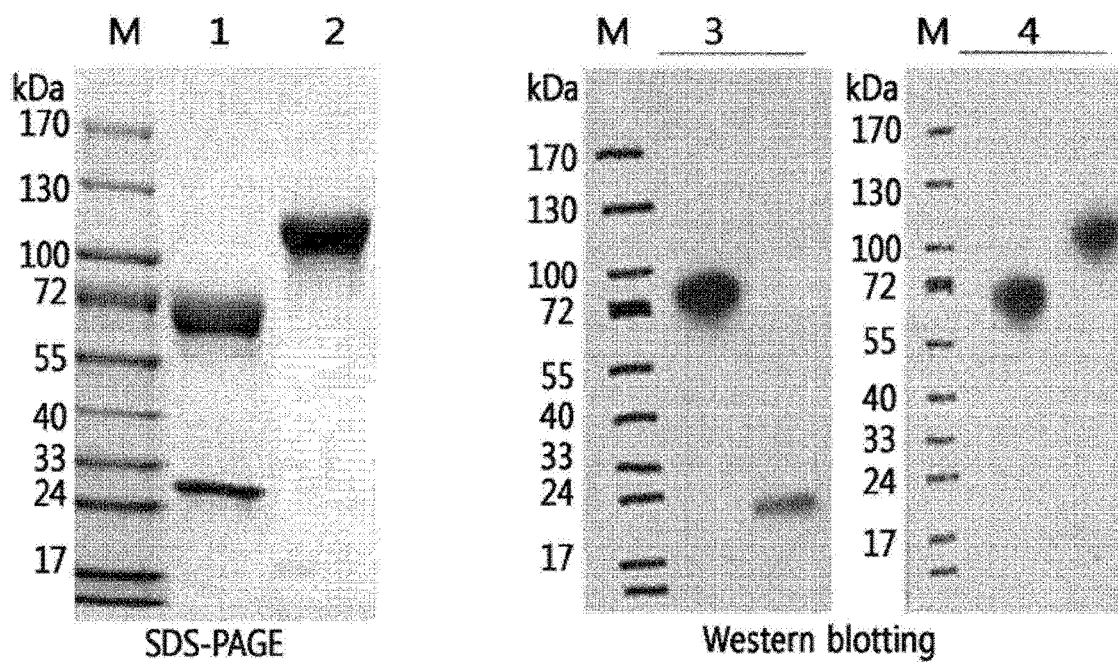
M. Size Marker
1. EPO-PEG-Fc reducing conditions
2. EPO-PEG-Fc non-reducing conditions
3. Use of anti-Fc antibody
(EPO-PEG-Fc non-reducing, reducing conditions)
4. Use of anti-EPO antibody
(EPO-PEG-Fc non-reducing, reducing conditions)

[Figure 1f]
(F) CA-Exendin4-PEG-Fc
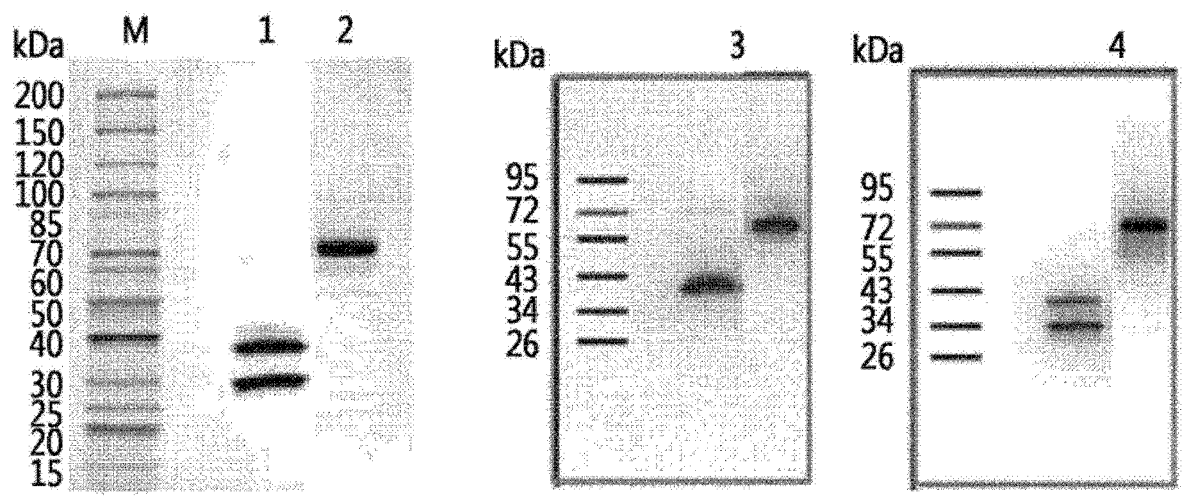
M. Size Marker
1. CA-Exendin4-PEG-Fc reducing conditions
2. CA-Exendin4-PEG-Fc non-reducing conditions
3. Use of anti-CA-Exendin4 antibody
(CA-Exendin4-PEG-Fc reducing,non-reducing conditions)
4. Use of anti-Fc antibody
(CA-Exendin4-PEG-Fc reducing,non-reducing conditions)

[Figure 1g]
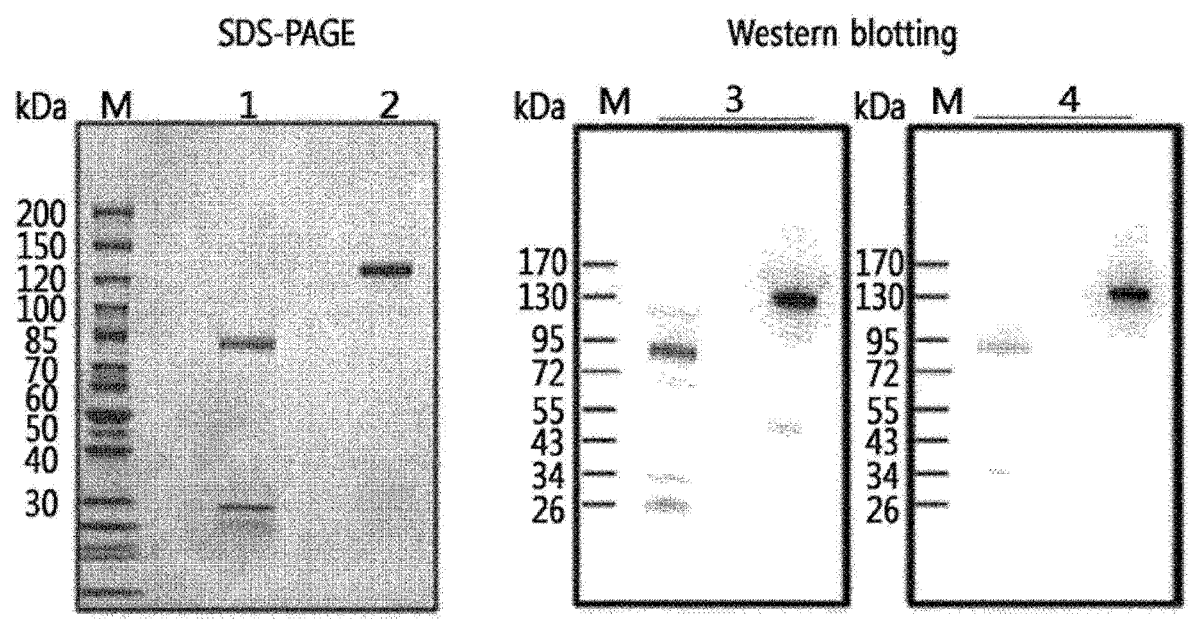
M. Size Marker
1. FacVII-PEG-Fc reducing conditions
2. FacVII-PEG-Fc non-reducing conditions
3. Use of anti-FacVII antibody (FacVII-PEG-Fc reducing, non-reducing conditions)
4. Use of anti-Fc antibody (FacVII-PEG-Fc reducing, non-reducing conditions)

【Figure 2a】
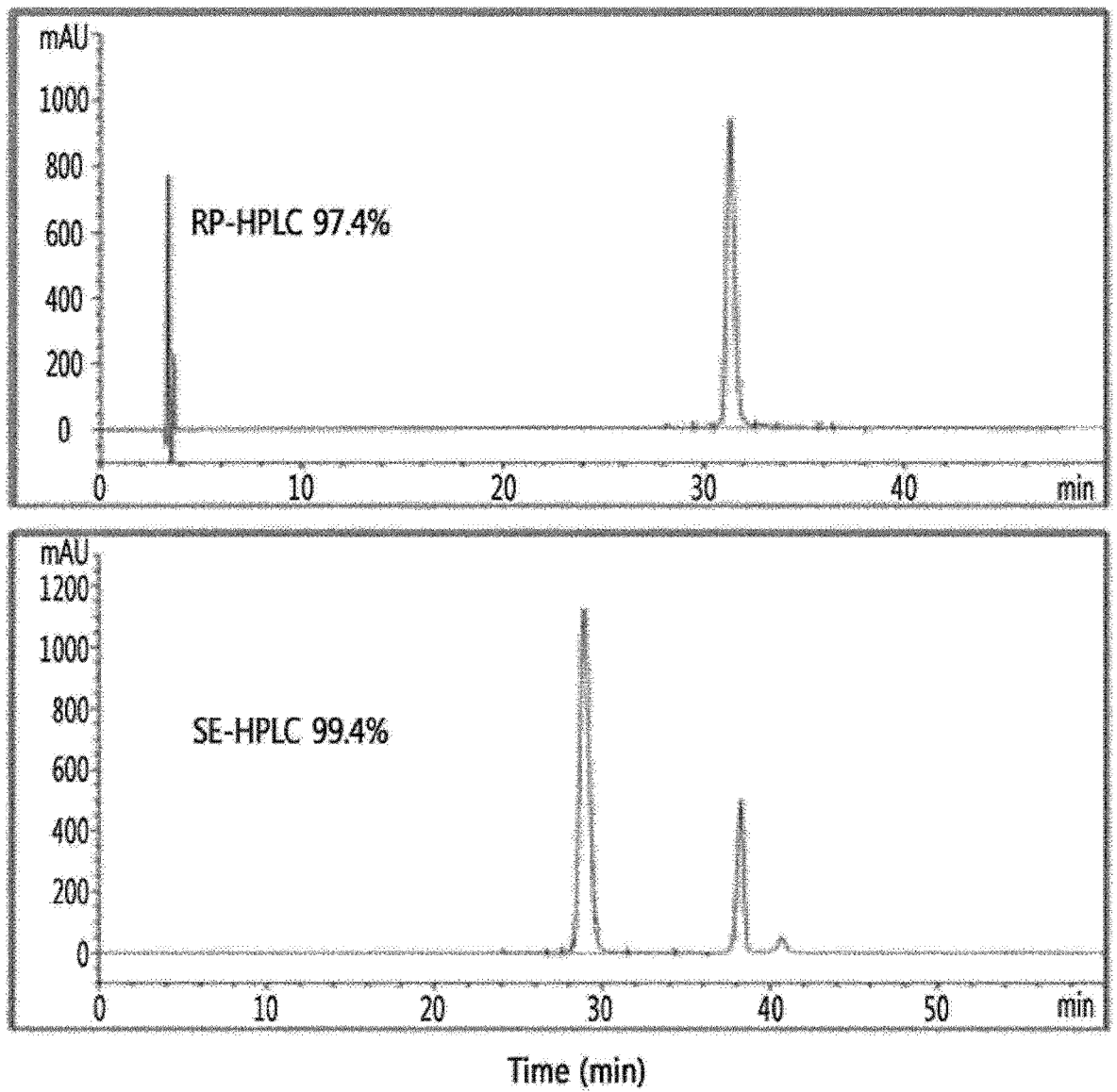

[Figure 2b]
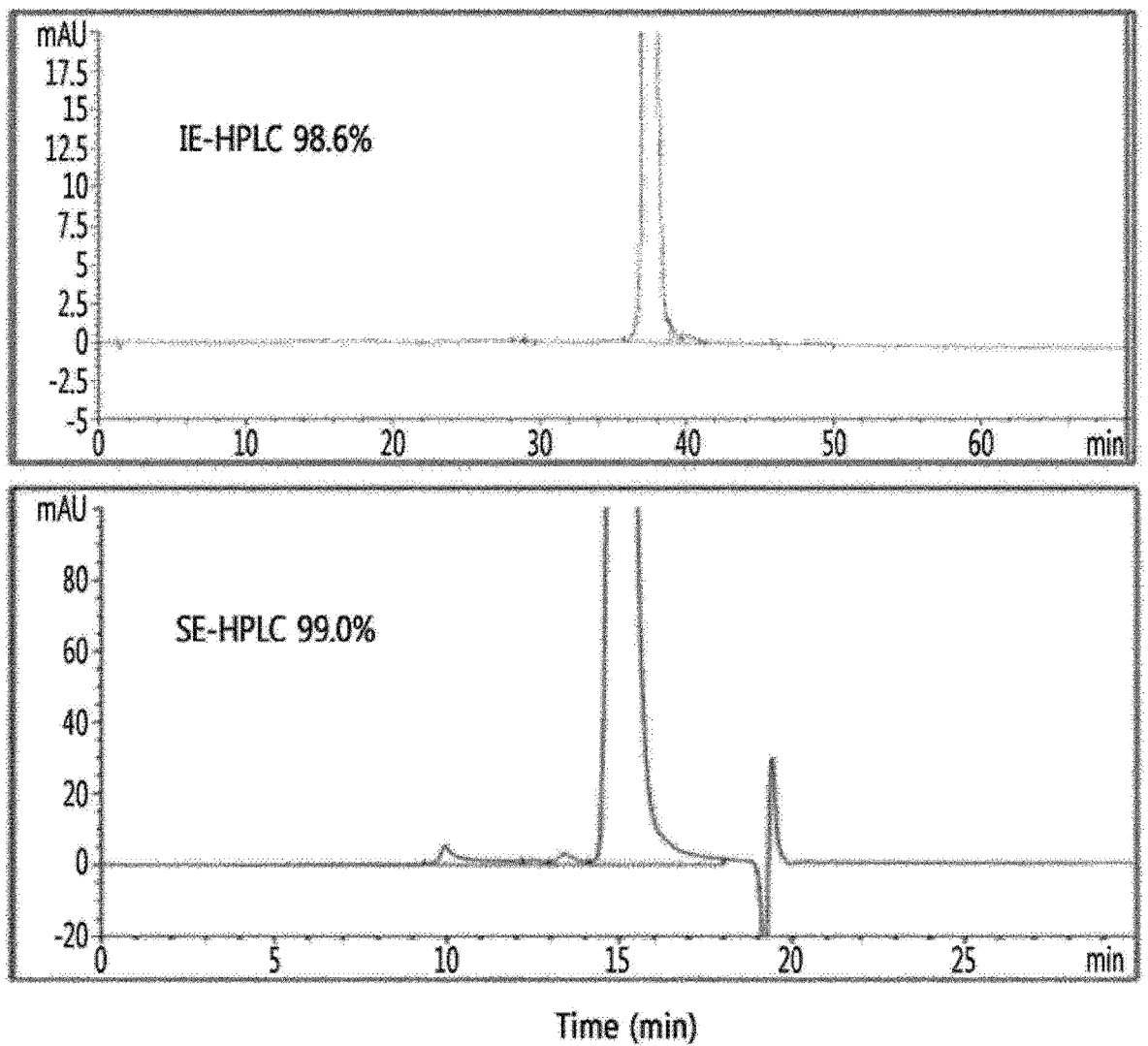
Time (min)

【Figure 2c】
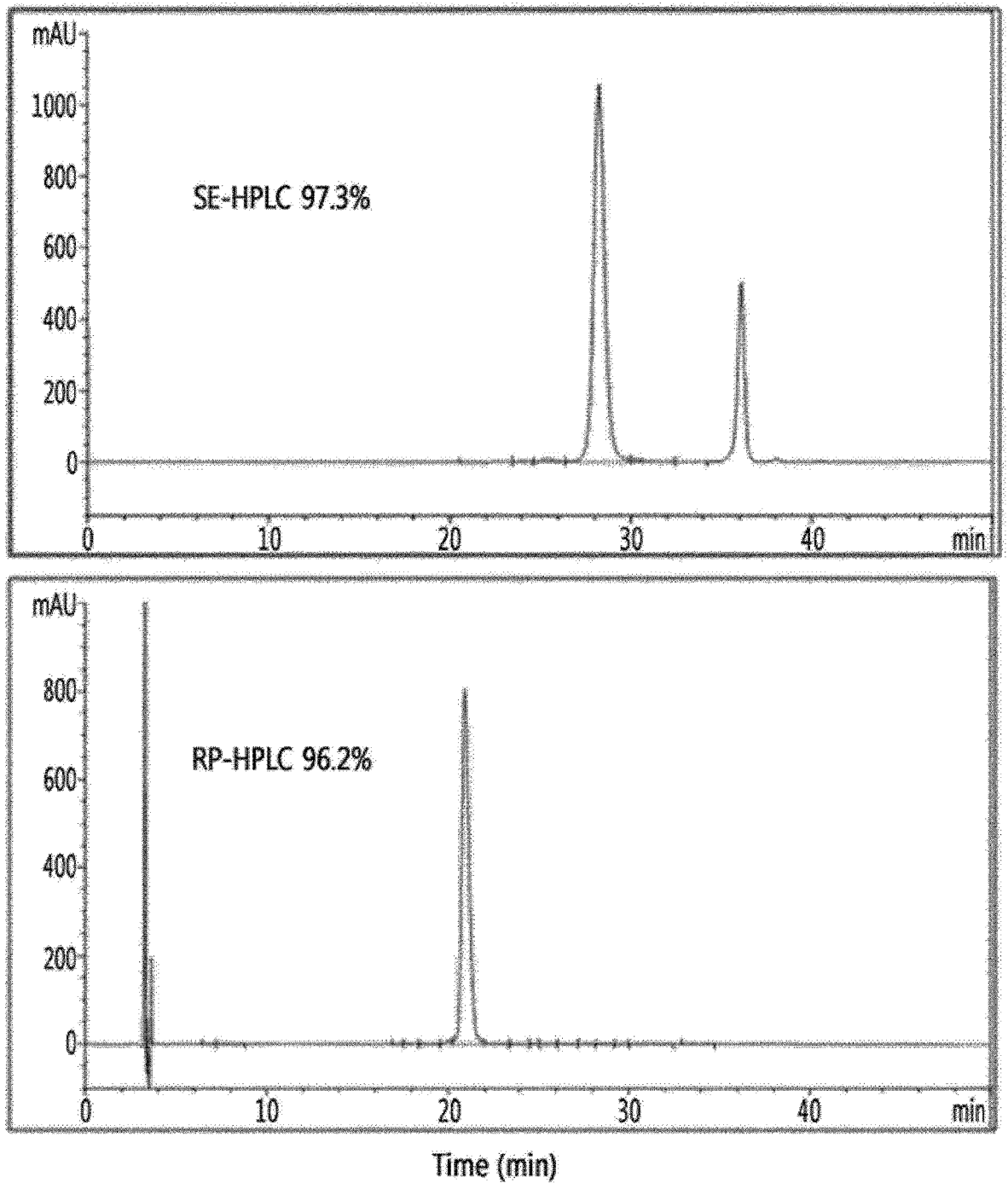

【Figure 2d】
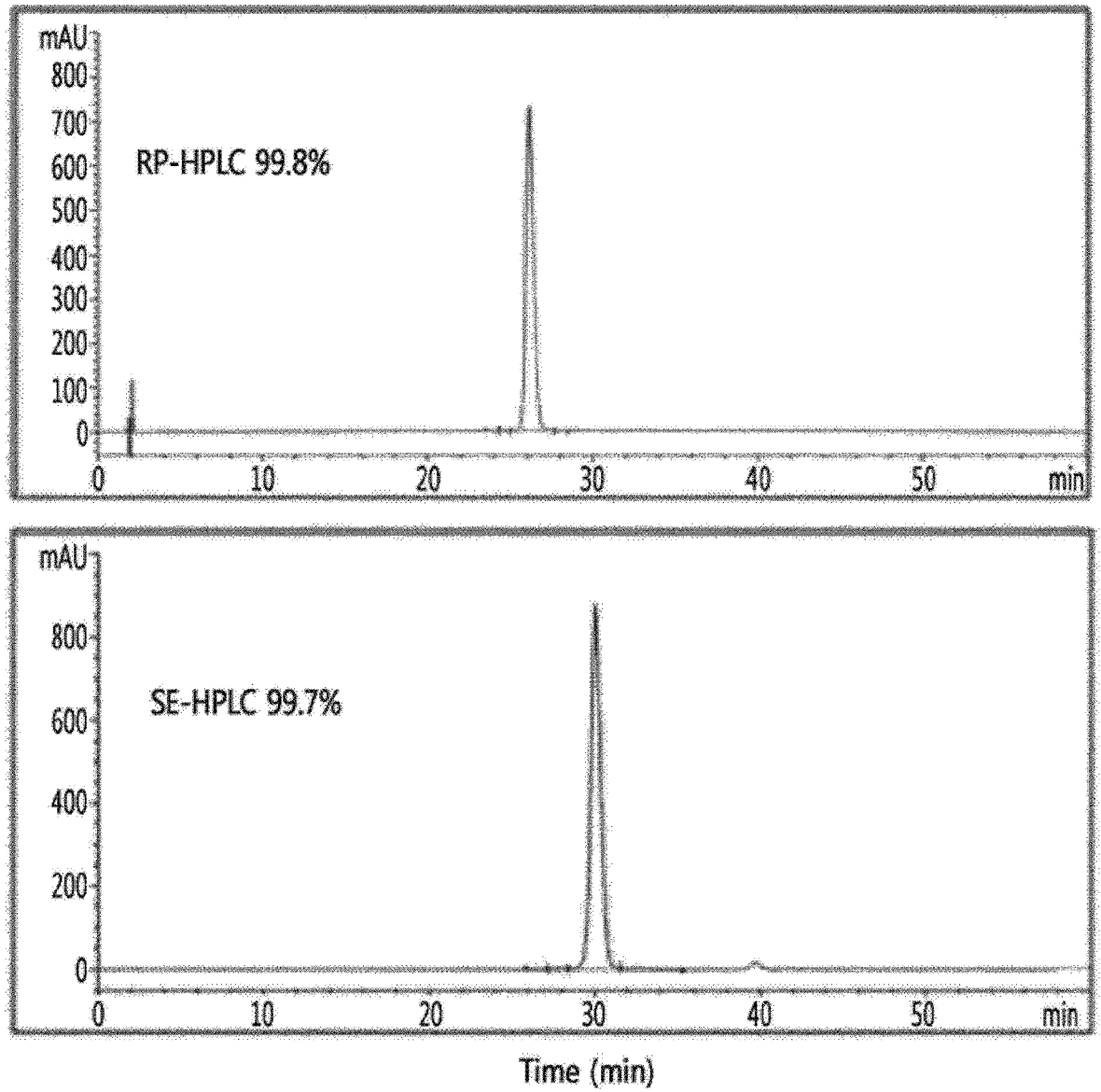

【Figure 2e】
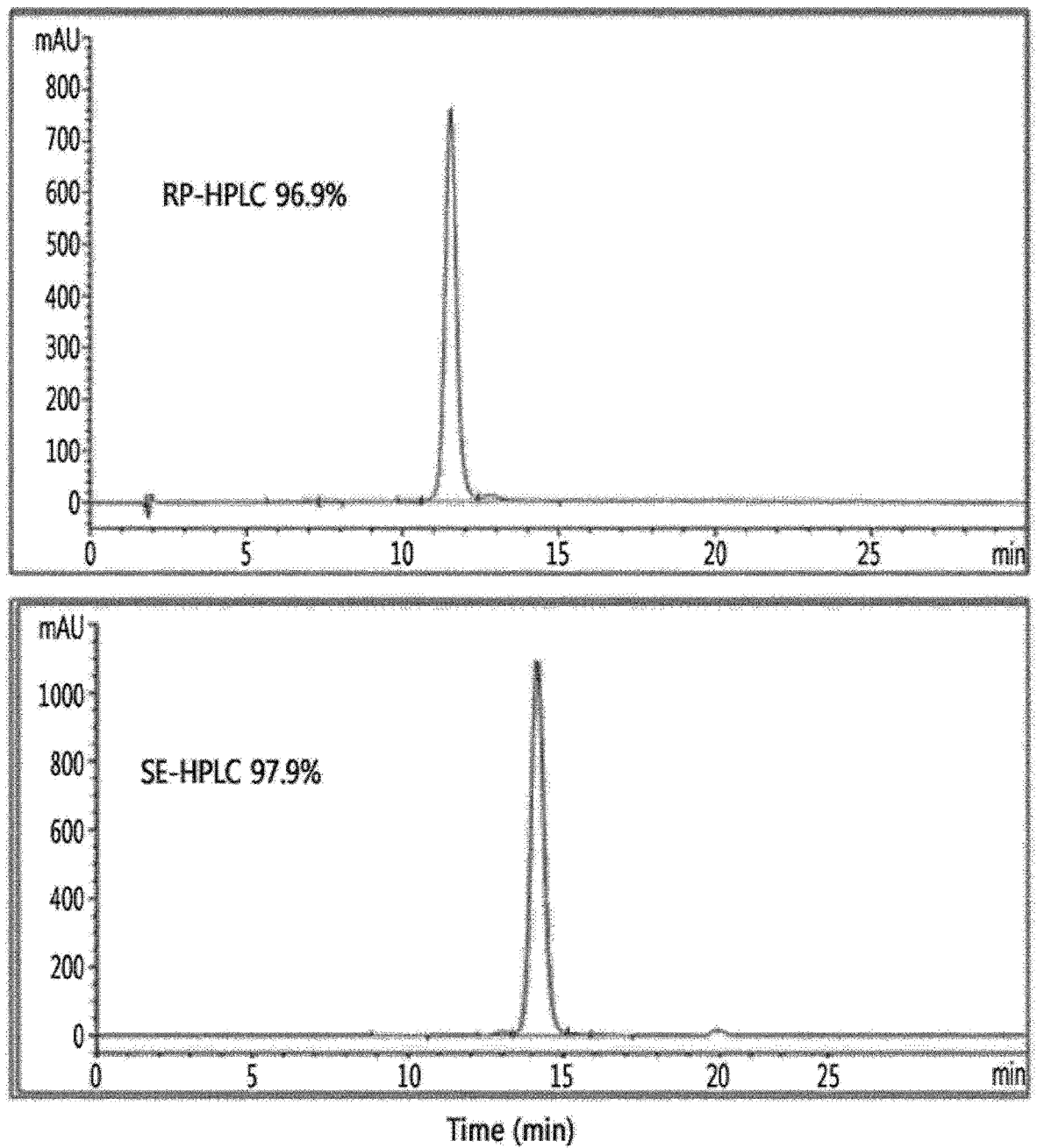

【Figure 2f】
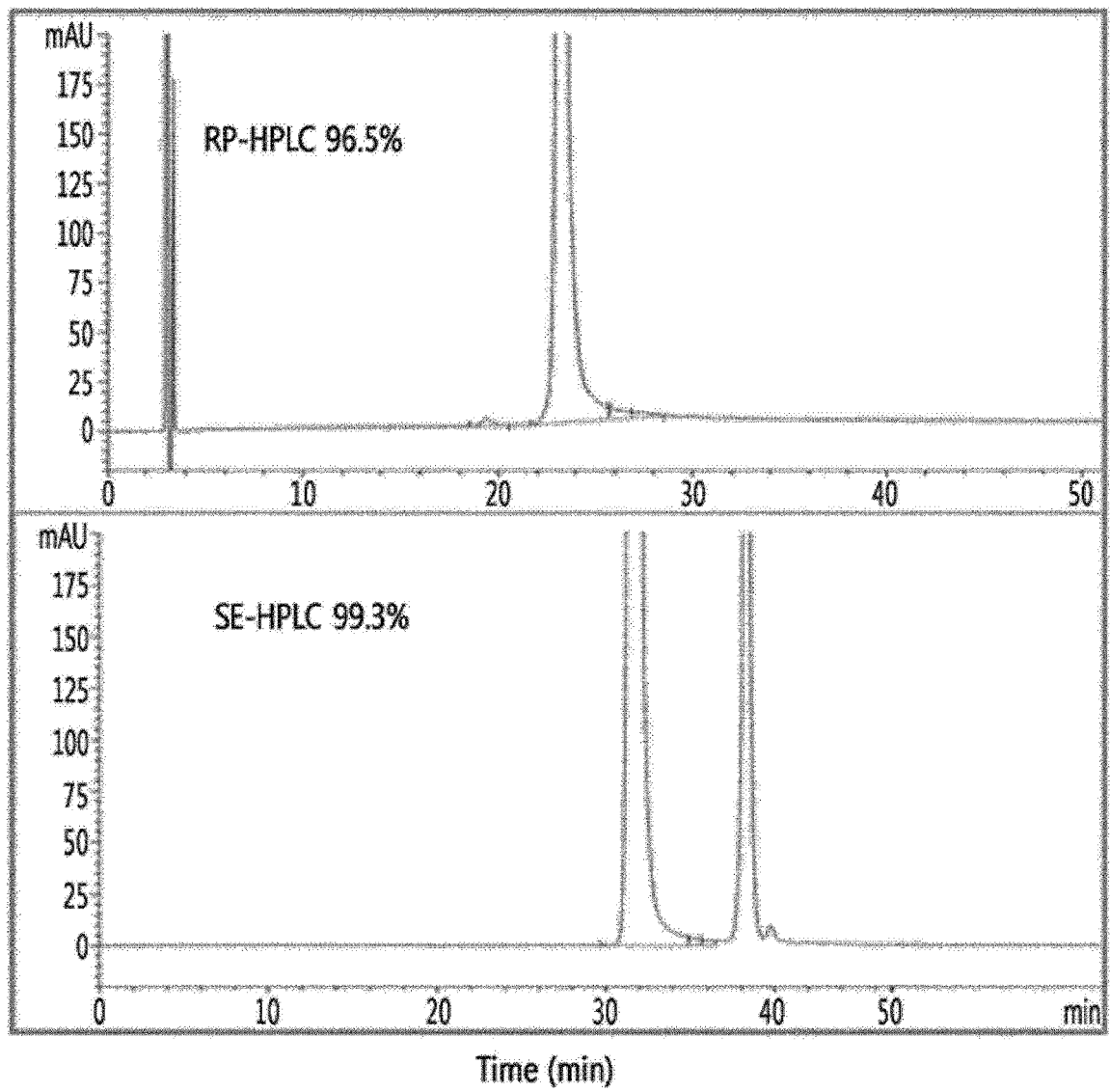
【Figure 3a】
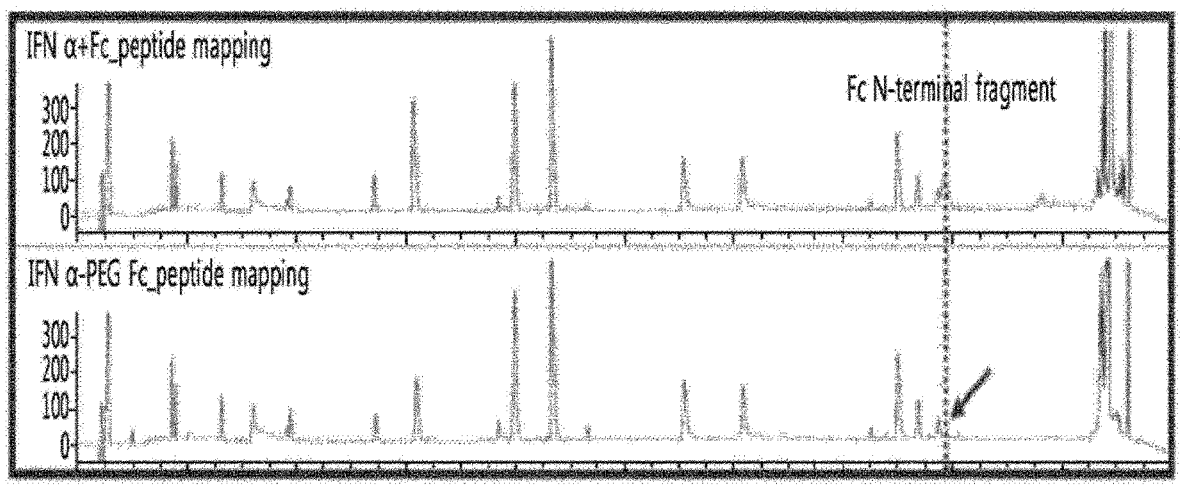

【Figure 3b】
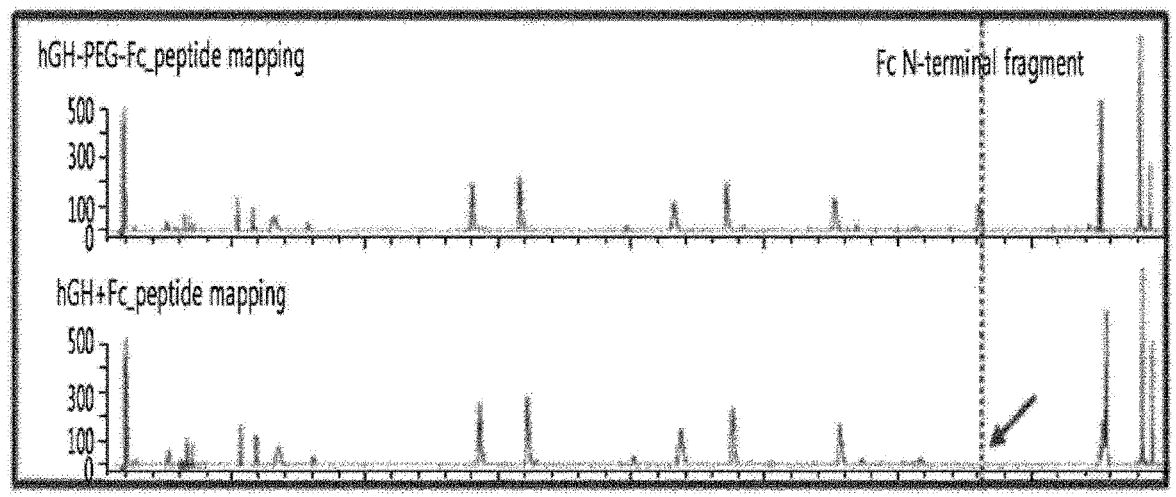
【Figure 3c】
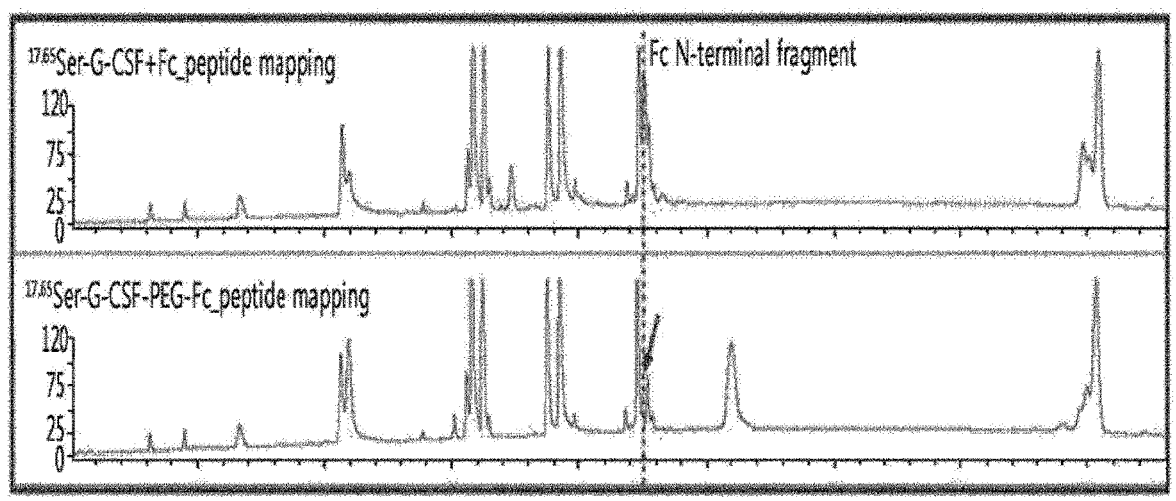
【Figure 3d】
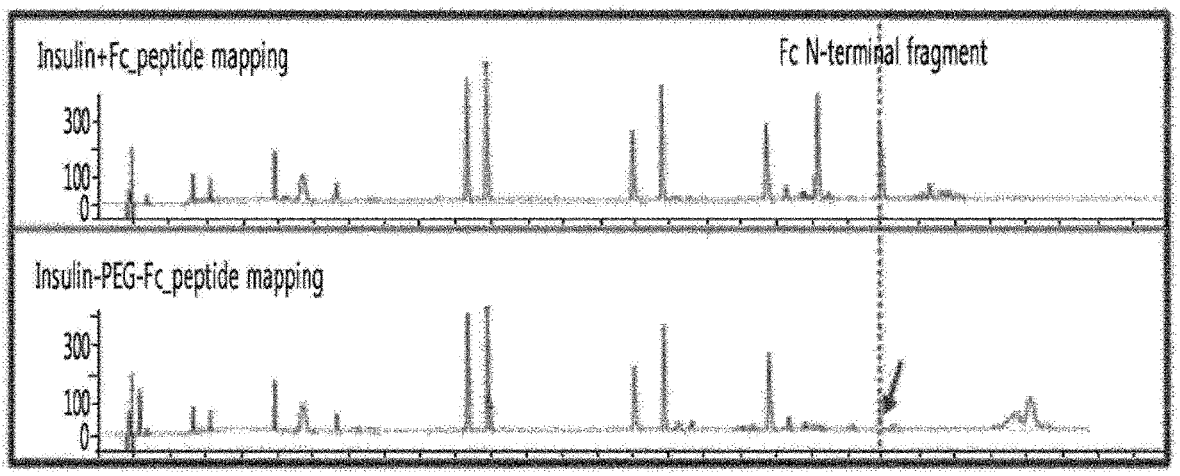

[Figure 3e]
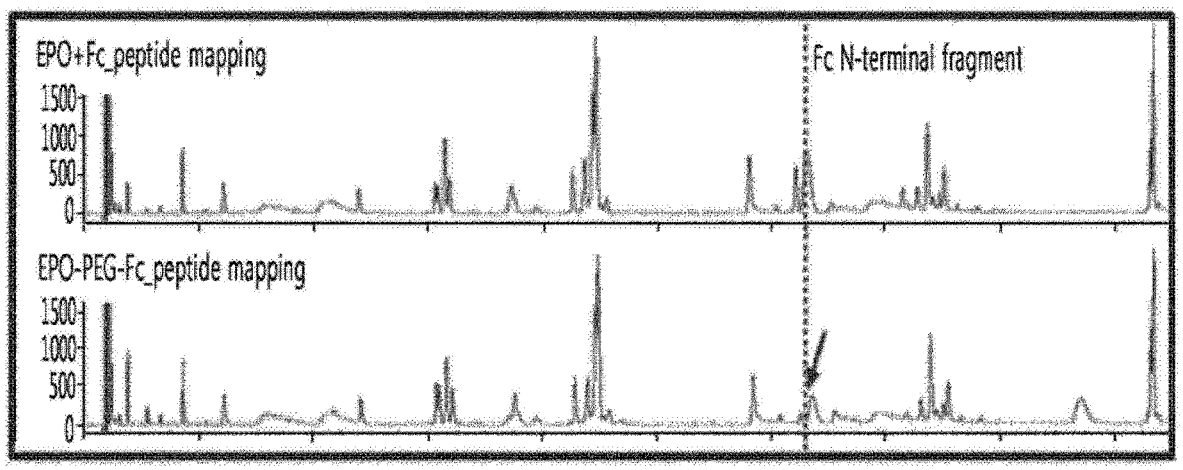
[Figure 3f]
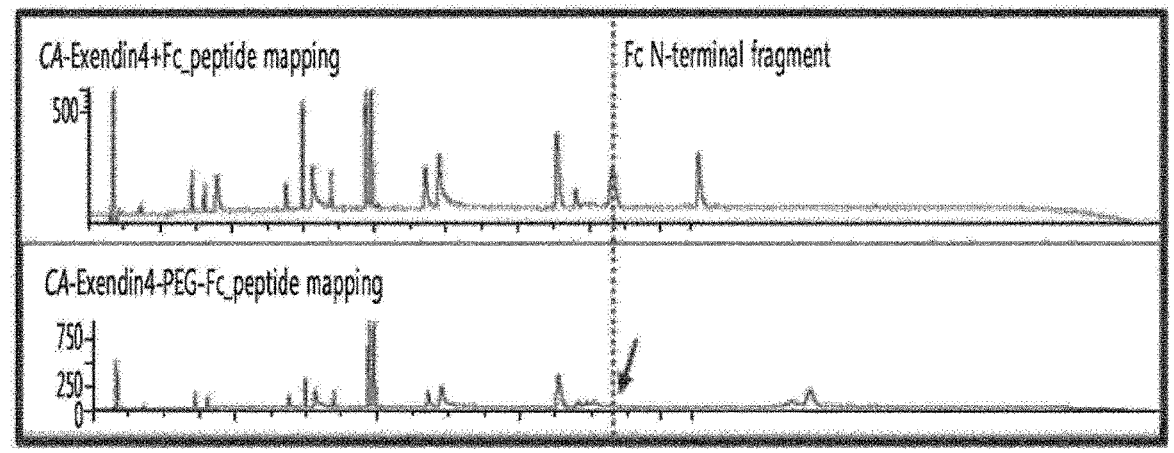

PROTEIN COMPLEX BY USE OF A SPECIFIC SITE OF AN IMMUNOGLOBULIN FRAGMENT FOR LINKAGE

CROSS REFERENCE TO RELATED APPLICATIONS

This application is a National Stage of International Application No. PCT/KR2016/010762 filed Sep. 26, 2016, claiming priority based on Korean Patent Application No. 10-2015-0135874, filed Sep. 24, 2015.

TECHNICAL FIELD

The present invention relates to a protein complex prepared by linking an immunoglobulin Fc region to a physiologically active polypeptide via a non-peptidyl polymer, in which the non-peptidyl polymer is specifically linked to a N-terminus of the immunoglobulin Fc region, a preparation method thereof, and a pharmaceutical composition including the same for improving in vivo duration and stability of the physiologically active polypeptide. Additionally, the present invention relates to a population of protein complexes which include the protein complexes prepared by the above method.

BACKGROUND ART

In general, polypeptides are easy to denature owing to their low stability, and are decomposed by proteolytic enzymes in blood to be readily removed through the kidney or liver. Therefore, in order to maintain the blood concentration and titer of a protein drug including a polypeptide as a pharmacologically active ingredient, it is necessary to frequently administer the protein drug to patients. However, in the case of protein drugs administered to patients primarily in the form of an injectable formulation, frequent injections to maintain the blood concentration of active polypeptides may cause excessive suffering in patients. To solve such problems, there has been constant effort to maximize pharmacological efficacy by increasing the blood stability of the protein drug and maintaining its blood concentration for a longer time. Such long-acting formulations of protein drugs are required to increase the stability of protein drugs and at the same time to maintain the potency of the drugs themselves at a sufficiently high level, as well as to cause no immune reaction in patients.

In the prior art, for stabilizing proteins and inhibiting contact with proteolytic enzymes and loss through the kidney, a method for chemically adding polymers having a high solubility such as polyethylene glycol (hereinafter, referred to as "PEG") to the surface of protein drugs has been used. It has been known that PEG is effective in stabilizing proteins and preventing the hydrolysis of proteins by non-specifically binding to a specific site or various sites of the target protein to increase the solubility thereof without causing any adverse side effects (Sada et al., *J. Fermentation Bioengineering* 71: 137-139, 1991). However, binding of PEG may increase stability of the protein but remarkably reduce the titer of the physiologically active protein. As a molecular weight of PEG is increased, its reactivity with the protein is also reduced, leading to low yield. Another problem which may be generated by binding of PEG to proteins is linkage isomerization of a conjugate, which is caused by competition of many possible linkage sites.

This is an important issue in the preparation of conjugate drugs using PEG, and there is a demand for homogeneous drugs prepared under conditions eliciting maximal efficacy and effect. If a large amount of related compounds generated by binding of PEG to a binding site which affects efficacy of the drug is included, an undesirable reduction in the efficacy may be caused.

DISCLOSURE

Technical Problem

The present inventors have studied a method capable of linking a physiologically active polypeptide conjugate at a site showing the highest efficacy by a process suitable for mass-production of the conjugate, and as a result, they have developed a method of preparing a high-purity conjugate with the highest efficacy by specifying a binding site of an immunoglobulin Fc fragment which is included as a carrier, thereby completing the present invention.

Technical Solution

An object of the present invention is to provide a protein complex prepared by linking a physiologically active polypeptide and an immunoglobulin Fc fragment via a non-peptidyl polymer, in which the non-peptidyl polymer is site-specifically linked to a N-terminus of the immunoglobulin Fc fragment.

Another object of the present invention is to provide a method of preparing the protein complex.

Still another object of the present invention is to provide a pharmaceutical composition for improving in vivo duration and stability of the physiologically active polypeptide, the composition including the protein complex as an active ingredient.

Advantageous Effects

The present invention relates to a protein complex with improved in vivo duration, which is prepared using a specific site during preparation of the protein complex. Particularly, the present invention relates to a protein complex in which a physiologically active polypeptide, a non-peptidyl polymer and a N-terminus of an immunoglobulin Fc region are linked to each other by a covalent bond, thereby improving in vivo duration of the physiologically active polypeptide. The protein complex prepared by the present invention may be applied to preparation of long-acting formulations of various physiologically active polypeptide drugs.

DESCRIPTION OF DRAWINGS

FIG. 1a shows results of SDS-PAGE and Western blotting of an IFNα-PEG-Fc complex which was prepared by N-terminal reaction of an immunoglobulin Fc region.

FIG. 1b shows results of SDS-PAGE and Western blotting of an hGH-PEG-Fc complex which was prepared by N-terminal reaction of an immunoglobulin Fc region.

FIG. 1c shows results of SDS-PAGE and Western blotting of a $^{17,65}$Ser-G-CSF-PEG-Fc complex which was prepared by N-terminal reaction of an immunoglobulin Fc region.

FIG. 1d shows results of SDS-PAGE and Western blotting of an insulin-PEG-Fc complex which was prepared by N-terminal reaction of an immunoglobulin Fc region.

FIG. 1e shows results of SDS-PAGE and Western blotting of an EPO-PEG-Fc complex which was prepared by N-terminal reaction of an immunoglobulin Fc region.

FIG. 1f shows results of SDS-PAGE and Western blotting of a CA-Exendin4-PEG-Fc complex which was prepared by N-terminal reaction of an immunoglobulin Fc region.

FIG. 1g shows results of SDS-PAGE and Western blotting of a FacVII-PEG-Fc complex which was prepared by N-terminal reaction of an immunoglobulin Fc region.

FIG. 2a shows results of IE-HPLC and SE-HPLC for analyzing purity of an IFNα-PEG-Fc complex which was prepared by N-terminal reaction of an immunoglobulin Fc region.

FIG. 2b shows results of IE-HPLC and SE-HPLC for analyzing purity of an hGH-PEG-Fc complex which was prepared by N-terminal reaction of an immunoglobulin Fc region.

FIG. 2c shows results of IE-HPLC and SE-HPLC for analyzing purity of a $^{17,65}$Ser-G-CSF-PEG-Fc complex which was prepared by N-terminal reaction of an immunoglobulin Fc region.

FIG. 2d shows results of IE-HPLC and SE-HPLC for analyzing purity of an insulin-PEG-Fc complex which was prepared by N-terminal reaction of an immunoglobulin Fc region.

FIG. 2e shows results of IE-HPLC and SE-HPLC for analyzing purity of an EPO-PEG-Fc complex which was prepared by N-terminal reaction of an immunoglobulin Fc region.

FIG. 2f shows results of IE-HPLC and SE-HPLC for analyzing purity of a CA-Exendin4-PEG-Fc complex which was prepared by N-terminal reaction of an immunoglobulin Fc region.

FIG. 3a shows a result of peptide mapping for analyzing Fc region N-terminal binding of an IFNα-PEG-Fc complex which was prepared by N-terminal reaction of an immunoglobulin Fc region.

FIG. 3b shows a result of peptide mapping for analyzing Fc region N-terminal binding of hGH-PEG-Fc complex which was prepared by N-terminal reaction of immunoglobulin Fc region.

FIG. 3c shows a result of peptide mapping for analyzing Fc region N-terminal binding of a $^{17,65}$Ser-G-CSF-PEG-Fc complex which was prepared by N-terminal reaction of an immunoglobulin Fc region.

FIG. 3d shows a result of peptide mapping for analyzing Fc region N-terminal binding of an insulin-PEG-Fc complex which was prepared by N-terminal reaction of an immunoglobulin Fc region.

FIG. 3e shows a result of peptide mapping for analyzing Fc region N-terminal binding of an EPO-PEG-Fc complex which was prepared by N-terminal reaction of an immunoglobulin Fc region.

FIG. 3f shows a result of peptide mapping for analyzing Fc region N-terminal binding of a CA-Exendin4-PEG-Fc complex which was prepared by N-terminal reaction of an immunoglobulin Fc region.

BEST MODE

In order to achieve the above objects, an aspect of the present invention provides a protein complex comprising a physiologically active polypeptide linked to an immunoglobulin Fc region via a non-peptidyl polymer, in which the non-peptidyl polymer is site-specifically linked to a N-terminus of the immunoglobulin Fc region.

A specific embodiment of the present invention provides the protein complex in which both ends of the non-peptidyl polymer are respectively linked to the physiologically active polypeptide and the immunoglobulin Fc region through reactive groups at both ends thereof by a covalent bond.

Another specific embodiment of the present invention provides the protein complex in which the immunoglobulin Fc region is aglycosylated.

Still another specific embodiment of the present invention provides the protein complex in which the immunoglobulin Fc region consists of one to four domains selected from the group consisting of CH1, CH2, CH3, and CH4 domains.

Still another specific embodiment of the present invention provides the protein complex in which the immunoglobulin Fc region further includes a hinge region.

Still another specific embodiment of the present invention provides the protein complex in which the immunoglobulin Fc region is an immunoglobulin Fc fragment derived from IgG, IgA, IgD, IgE, or IgM.

Still another specific embodiment of the present invention provides the protein complex in which each domain of the immunoglobulin Fc fragment is a hybrid of domains and each domain has a different origin derived from immunoglobulins selected from the group consisting of IgG, IgA, IgD, IgE, and IgM.

Still another specific embodiment of the present invention provides the protein complex in which the immunoglobulin Fc fragment is a dimer or multimer consisting of single chain immunoglobulins comprising domains having the same origin.

Still another specific embodiment of the present invention provides the protein complex in which the immunoglobulin Fc fragment is an IgG4 Fc fragment.

Still another specific embodiment of the present invention provides the protein complex in which the immunoglobulin Fc fragment is a human aglycosylated IgG4 Fc fragment.

Still another specific embodiment of the present invention provides the protein complex in which the non-peptidyl polymer is selected from the group consisting of polyethylene glycol, polypropylene glycol, an ethylene glycol-propylene glycol copolymer, polyoxyethylated polyol, polyvinyl alcohol, polysaccharide, dextran, polyvinyl ethyl ether, a biodegradable polymer, a lipid polymer, chitin, hyaluronic acid, and a combination thereof.

Still another specific embodiment of the present invention provides the protein complex in which the non-peptidyl polymer is polyethylene glycol.

Still another specific embodiment of the present invention provides the protein complex in which the reactive group of the non-peptidyl polymer is selected from the group consisting of an aldehyde group, a maleimide group, and a succinimide derivative.

Still another specific embodiment of the present invention provides the protein complex in which the aldehyde group is a propionaldehyde group, or a butyraldehyde group.

Still another specific embodiment of the present invention provides the protein complex in which the succinimide derivative is succinimidyl carboxymethyl, succinimidyl valerate, succinimidyl methylbutanoate, succinimidyl methylpropionate, succinimidyl butanoate, succinimidyl propionate, N-hydroxysuccinimide, or succinimidyl carbonate.

Still another specific embodiment of the present invention provides the protein complex in which the non-peptidyl polymer has an aldehyde group as a reactive group at both ends.

Still another specific embodiment of the present invention provides the protein complex in which the non-peptidyl polymer has an aldehyde group and a maleimide group as a reactive group at both ends, respectively.

Still another specific embodiment of the present invention provides the protein complex in which the non-peptidyl polymer has an aldehyde group and a succinimide group as a reactive group at both ends, respectively.

Still another specific embodiment of the present invention provides the protein complex in which each end of the non-peptidyl polymer is linked to the N-terminus of the immunoglobulin Fc region; and the N-terminus, C-terminus, or a free reactive group of a lysine residue, a histidine residue, or a cysteine residue of the physiologically active polypeptide, respectively.

Still another specific embodiment of the present invention provides the protein complex in which the physiologically active polypeptide is selected from the group consisting of a hormone, a cytokine, an enzyme, an antibody, a growth factor, a transcription factor, a blood coagulation factor, a vaccine, a structural protein, a ligand protein, and a receptor.

Still another specific embodiment of the present invention provides the protein complex in which the physiologically active polypeptide is selected from the group consisting of human growth hormone, growth hormone-releasing hormone, growth hormone-releasing peptide, interferons, interferon receptors, colony-stimulating factors, glucagon-like peptides (GLP-1, etc.), exendins (Exendin4, etc.), oxyntomodulin, G-protein-coupled receptors, interleukins, interleukin receptors, enzymes, interleukin-coupled proteins, cytokine-coupled proteins, macrophage activating factor, macrophage peptide, B cell factor, T cell factor, protein A, allergy inhibiting factor, cell necrosis glycoprotein, immunotoxin, lymphotoxin, tumor necrosis factor, tumor suppressor, transforming growth factor, α-1 antitrypsin, albumin, α-lactalbumin, apolipoprotein-E, erythropoietin, glycosylated erythropoietin, angiopoietins, hemoglobin, thrombin, thrombin receptor activating peptides, thrombomodulin, blood coagulation factors VII, VIIa, VIII, IX and XIII, plasminogen activator, fibrin-binding peptide, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone morphogenetic growth factor, bone morphogenetic stimulating protein, calcitonin, insulin, atriopeptin, cartilage-inducing factor, elcatonin, connective tissue-activating factor, tissue factor pathway inhibitor, follicle-stimulating hormone, luteinizing hormone, luteinizing hormone-releasing hormone, nerve growth factors, parathyroid hormone, relaxin, secretin, somatomedin, insulin-like growth factor, adrenocortical hormone, glucagon, cholecystokinin, pancreatic polypeptides, gastrin-releasing peptides, corticotropin-releasing factor, thyroid stimulating hormone, autotaxin, lactoferrin, myostatin, receptors, receptor antagonist, cell surface antigen, virus-derived vaccine antigen, monoclonal antibody, polyclonal antibody, antibody fragments, and a derivative thereof.

Still another specific embodiment of the present invention provides the protein complex in which the physiologically active polypeptide is human growth hormone, interferon-alpha, granulocyte colony-stimulating factor, erythropoietin, blood coagulation factor, insulin, oxyntomodulin, glucagon-like peptides, exendins, and a derivative thereof.

Another aspect of the present invention provides a method of preparing the protein complex, the method comprising:

(a) preparing a protein complex by linking at least one non-peptidyl polymer having a reactive group at both ends, at least one physiologically active polypeptide, and at least one immunoglobulin Fc region by a covalent bond, and (b) isolating the protein complex, essentially including the covalently linked physiologically active polypeptide, non-peptidyl polymer, and immunoglobulin Fc region prepared in step (a), in which the non-peptidyl polymer is linked to the N-terminus of the immunoglobulin Fc fragment.

A specific embodiment of the present invention provides the preparation method, in which step (a) comprises:

(a1) preparing a conjugate by linking one end of the non-peptidyl polymer to the immunoglobulin Fc region or the physiologically active polypeptide by a covalent bond; and (a2) isolating the conjugate prepared in step (a1) and linking the other end of the non-peptidyl polymer of the isolated conjugate to the other of the immunoglobulin Fc region and the physiologically active polypeptide by a covalent bond.

Another specific embodiment of the present invention provides the preparation method in which in step (a1), the reaction mole ratio between the physiologically active polypeptide and the non-peptidyl polymer is in the range from 1:1 to 1:30, and the reaction mole ratio between the immunoglobulin Fc fragment and the non-peptidyl polymer is in the range from 1:1 to 1:20.

Still another specific embodiment of the present invention provides the preparation method in which step (a1) is performed in a pH condition from 4.0 to 9.0.

Still another specific embodiment of the present invention provides the preparation method in which step (a1) is performed at a temperature from 4.0° C. to 25° C.

Still another specific embodiment of the present invention provides the preparation method in which in step (a1), the reaction concentration of the immunoglobulin Fc region or physiologically active polypeptide is in the range from 0.1 mg/mL to 100 mg/mL.

Still another specific embodiment of the present invention provides the preparation method in which in step (a2), the reaction mole ratio between the conjugate and the immunoglobulin Fc region or the physiologically active polypeptide is in the range from 1:0.1 to 1:20.

Still another specific embodiment of the present invention provides the preparation method in which step (a2) is performed in a pH condition from 4.0 to 9.0.

Still another specific embodiment of the present invention provides the preparation method in which step (a2) is performed at a temperature from 4.0° C. to 25° C.

Still another specific embodiment of the present invention provides the preparation method in which in step (a2), the concentration of the immunoglobulin Fc region or physiologically active polypeptide is in the range from 0.1 mg/mL to 100 mg/mL.

Still another specific embodiment of the present invention provides the preparation method in which step (a1) and step (a2) are performed in the presence of a reducing agent.

Still another specific embodiment of the present invention provides the preparation method in which the reducing agent is selected from the group consisting of sodium cyanoborohydride (NaCNBH$_3$), sodium borohydride, dimethylamine borate, and pyridine borate.

Still another specific embodiment of the present invention provides the preparation method in which in step (a2), the isolation is performed by a single or combined purification method selected from the group consisting of anion exchange chromatography, cation exchange chromatography, hydrophobic chromatography, affinity chromatography, and size exclusion chromatography.

Still another specific embodiment of the present invention provides the preparation method in which the functional group of the anion exchange chromatography resin is any one selected from the group consisting of quaternary ammonium (Q), quaternary aminoethyl (QAE), diethylaminoethyl (DEAE), polyethylene amine (PEI), dimethylaminomethyl (DMAE), and trimethylaminoethyl (TMAE).

Still another specific embodiment of the present invention provides the preparation method in which the functional group of the cation exchange chromatography resin is any one selected from the group consisting of methylsulfonate (S), sulfopropyl (SP), carboxymethyl (CM), sulfoethyl (SE), and polyaspartic acid.

Still another specific embodiment of the present invention provides the preparation method in which the functional group of the hydrophobic chromatography resin is any one selected from the group consisting of phenyl, octyl, (iso) propyl, butyl, and ethyl.

Still another specific embodiment of the present invention provides the preparation method in which the functional group of the affinity chromatography resin is any one selected from the group consisting of protein A, heparin, blue, benzamidine, metal ions (cobalt, nickel, and copper), and an antibody to a part or the entirety of constituting components of the protein complex, in which both ends of the non-peptidyl polymer are respectively conjugated to the immunoglobulin Fc region and the physiologically active polypeptide.

Still another specific embodiment of the present invention provides the preparation method in which the resin of the size exclusion chromatography is selected from the group consisting of Superdex, Sephacryl, Superpose, and Sephadex.

Still another specific embodiment of the present invention provides the preparation method in which the isolating the protein complex of step (b) is performed by a single or combined method selected from the group consisting of anion exchange chromatography, cation exchange chromatography, hydrophobic chromatography, affinity chromatography, and size exclusion chromatography.

Still another specific embodiment of the present invention provides the preparation method in which the functional group of the anion exchange chromatography resin is any one selected from the group consisting of quaternary ammonium (Q), quaternary aminoethyl (QAE), diethylaminoethyl (DEAE), polyethylene amine (PEI), dimethylaminomethyl (DMAE), and trimethylaminoethyl (TMAE).

Still another specific embodiment of the present invention provides the preparation method in which the functional group of the cation exchange chromatography resin is any one selected from the group consisting of methylsulfonate (S), sulfopropyl (SP), carboxymethyl (CM), sulfoethyl (SE), and polyaspartic acid.

Still another specific embodiment of the present invention provides the preparation method in which the functional group of the hydrophobic chromatography resin is any one selected from the group consisting of phenyl, octyl, (iso) propyl, butyl, and ethyl.

Still another specific embodiment of the present invention provides the preparation method in which the functional group of the affinity chromatography resin is any one selected from the group consisting of protein A, heparin, blue, benzamidine, metal ions (cobalt, nickel, and copper), an antibody to a part or the entirety of constituting components of the protein complex, in which both ends of the non-peptidyl polymer are respectively conjugated to the immunoglobulin Fc region and the physiologically active polypeptide.

Still another specific embodiment of the present invention provides the preparation method in which the resin of the size exclusion chromatography is selected from the group consisting of Superdex, Sephacryl, Superpose, and Sephadex.

Still another specific embodiment of the present invention provides the preparation method in which step (b) is to isolate the protein complex in which the non-peptidyl polymer and an immunoglobulin Fc region, constituting a protein complex, are linked through the N-terminus of the immunoglobulin Fc region.

Still another aspect of the present invention provides a method of preparing the position-specific protein complex, the method comprising:

(a') preparing a conjugate by linking one end of the non-peptidyl polymer to the immunoglobulin Fc region or the physiologically active polypeptide by a covalent bond, which is performed in a pH condition from 4.0 to 9.0;

(b') isolating the conjugate prepared in step (a') and linking the other end of the non-peptidyl polymer of the isolated conjugate to the other of the immunoglobulin Fc region and the physiologically active polypeptide by a covalent bond, which is performed in a pH condition from 4.0 to 9.0; and (c') isolating the protein complex, essentially including the covalently linked physiologically active polypeptide, non-peptidyl polymer, and immunoglobulin Fc region prepared in step (b'), in which the non-peptidyl polymer is linked to the N-terminus of the immunoglobulin Fc fragment.

In particular, an important condition for a reaction rate in binding between the non-peptidyl polymer and the N-terminus of the immunoglobulin Fc region is pH, and the site-specific binding may occur well at a pH value below neutral pH, that is, below pH 7.0.

The linking of the non-peptidyl polymer to the N-terminus of the immunoglobulin Fc region is performed at a pH value below neutral pH, but suitably performed at a weak acidic to acidic pH which does not denature a tertiary structure or activity of the protein, but is not limited thereto. As a non-limiting example, the immunoglobulin Fc region used in the present invention has an amino acid sequence of SEQ ID NO: 1 and it was confirmed to have N-terminal specificity at a weak basic condition of about pH 8.2 (Example 5).

That is, when a general immunoglobulin Fc region is used, the reaction rate of a specific binding of N-terminal of the immunoglobulin Fc region and the non-peptidyl polymer is increased at a pH below neutral pH. However, when an immunoglobulin Fc region mutated to have a lower pH sensitivity is used, the reaction rate of the binding may not be restricted to the condition.

Still another aspect of the present invention provides a method of preparing the protein complex, the method comprising:

(a') preparing a conjugate by linking one end of the non-peptidyl polymer to any one of the immunoglobulin Fc region and the physiologically active polypeptide by a covalent bond, in which the reaction mole ratio between the physiologically active polypeptide and the non-peptidyl polymer is in the range from 1:1 to 1:30, and the reaction mole ratio between the immunoglobulin Fc region and the non-peptidyl polymer is in the range from 1:1 to 1:20, a reducing agent is contained in the range from 1 mM to 100 mM, and the reaction is performed in the condition of pH from 4.0 to 9.0, at a temperature from 4.0° C. to 25° C., and the reaction concentration of the immunoglobulin Fc region or physiologically active polypeptide is in the range from 0.1 mg/mL to 100 mg/mL;

(b') isolating the conjugate prepared in step (a') and linking the other end of the non-peptidyl polymer of the isolated conjugate to the other of the immunoglobulin Fc region and the physiologically active polypeptide by a covalent bond, in which the reaction mole ratio between the conjugate and the immunoglobulin Fc region or the physiologically active polypeptide is in the range from 1:0.1 to 1:20, a reducing agent is contained in the range from 1 mM to 100 mM, and the reaction is performed in the condition of pH from 4.0 to 9.0, at a temperature from 4.0° C. to 25° C., and the reaction concentration of the immunoglobulin Fc region or physiologically active polypeptide is in the range from 0.1 mg/mL to 100 mg/mL; and (c') isolating the protein complex, essentially comprising the covalently linked physiologically active polypeptide, non-peptidyl polymer, and immunoglobulin Fc region prepared in step (b'), in which the non-peptidyl polymer is linked to the N-terminus of the immunoglobulin Fc fragment.

Still another specific embodiment of the present invention provides a method for preparing the protein complex with N-terminal selectivity of 90% or higher.

Still another aspect of the present invention provides a pharmaceutical composition for improving in vivo duration and stability of the physiologically active polypeptide comprising the protein complex as an active ingredient.

A specific embodiment of the present invention provides a composition comprising the protein complex in an amount of 90% or higher.

Still another aspect of the present invention provides a population of protein complexes comprising the protein complex prepared according to the above method for preparing a protein complex, in an amount of 90% or higher.

Hereinafter, the present invention will be described in detail.

An aspect of the present invention provides a protein complex prepared by linking a physiologically active polypeptide and an immunoglobulin Fc region via a non-peptidyl polymer, in which the non-peptidyl polymer is site-specifically linked to a N-terminus of the immunoglobulin Fc region.

As used herein, the term "protein complex" or "complex" refers to a structure in which at least one physiologically active polypeptide, at least one non-peptidyl polymer having a reactive group at both ends thereof, and at least one immunoglobulin Fc region are linked to each other via a covalent bond. Further, a structure in which only two molecules selected from the physiologically active polypeptide, the non-peptidyl polymer, and the immunoglobulin Fc region are linked to each other via a covalent bond is called "conjugate" in order to distinguish it from the "complex".

The protein complex of the present invention may be a protein complex in which the non-peptidyl polymer is linked to the physiologically active polypeptide and the immunoglobulin Fc region through reactive groups at both ends thereof by a covalent bond, respectively.

As used herein, the term "physiologically active polypeptide", "physiologically active protein", "active protein", or "protein drug" refers to a polypeptide or a protein having some kind of antagonistic activity to a physiological event in vivo, and these terms may be used interchangeably.

As used herein, the term "non-peptidyl polymer" refers to a biocompatible polymer including two or more repeating units which are linked to each other by any covalent bond excluding a peptide bond, but is not limited thereto.

As used herein, the term "immunoglobulin Fc region" refers to a region of an immunoglobulin molecule, except for the variable regions of the heavy and light chains, the heavy-chain constant region 1 ($C_H1$) and the light-chain constant region 1 ($C_L1$) of an immunoglobulin. The immunoglobulin Fc region may further include a hinge region at the heavy-chain constant region. In particular, the immunoglobulin Fc region of the present invention may be a fragment including a part or all of the Fc region, and in the present invention, the immunoglobulin Fc region may be used interchangeably with an immunoglobulin fragment.

A native Fc has a sugar chain at position Asn297 of heavy-chain constant region 1, but E. coli-derived recombinant Fc is expressed as an aglycosylated form. The removal of sugar chains from Fc results in a decrease in binding affinity of Fc gamma receptors 1, 2, and 3 and complement (c1q) to heavy-chain constant region 1, leading to a decrease or loss in antibody-dependent cell-mediated cytotoxicity or complement-dependent cytotoxicity.

As used herein, the term "immunoglobulin constant region" may refer to an Fc fragment including heavy-chain constant region 2 (CH2) and heavy-chain constant region 3 (CH3) (or containing heavy-chain constant region 4 (CH4)), except for the variable regions of the heavy and light chains, the heavy-chain constant region 1 (CH1) and the light-chain constant region (CL) of an immunoglobulin, and may further include a hinge region at the heavy chain constant region. Further, the immunoglobulin constant region of the present invention may be an extended immunoglobulin constant region including a part or all of the Fc region including the heavy-chain constant region 1 (CH1) and/or the light-chain constant region (CL), except for the variable regions of the heavy and light chains of an immunoglobulin, as long as it has a physiological function substantially similar to or better than the native protein. Also, it may be a region having a deletion in a relatively long portion of the amino acid sequence of CH2 and/or CH3. That is, the immunoglobulin constant region of the present invention may include (1) a CH1 domain, a CH2 domain, a CH3 domain, and a CH4 domain, (2) a CH1 domain and a CH2 domain, (3) a CH1 domain and a CH3 domain, (4) a CH2 domain and a CH3 domain, (5) a combination of one or more domains of the constant region and an immunoglobulin hinge region (or a portion of the hinge region), and (6) a dimer of each domain of the heavy-chain constant regions and the light-chain constant region. An immunoglobulin constant region including the immunoglobulin Fc fragment is a biodegradable polypeptide which can be metabolized in vivo, so that it can safely be used as a drug carrier. In addition, an immunoglobulin Fc fragment is more advantageous in terms of production, purification, and yield of a complex than an entire immunoglobulin molecule, owing to its relatively low molecular weight. Further, since it is devoid of Fab, which exhibits high non-homogeneity due to the difference in amino acid sequence from one antibody to another, it is expected to significantly enhance homogeneity and to reduce the possibility of inducing blood antigenicity.

Meanwhile, the immunoglobulin constant region may originate from humans or animals, such as cows, goats, pigs, mice, rabbits, hamsters, rats, guinea pigs, etc., and may preferably be of human origin. In addition, the immunoglobulin constant region may be selected from constant regions derived from IgG, IgA, IgD, IgE, IgM, or combinations or hybrids thereof, preferably, derived from IgG or IgM, which are the most abundant thereof in human blood, and most preferably, derived from IgG, which is known to improve the half-life of ligand-binding proteins. In the present invention, the immunoglobulin Fc region may be a dimer or multimer consisting of single-chain immunoglobulins of domains of the same origin.

As used herein, the term "combination" means that polypeptides encoding single chain immunoglobulin constant regions (preferably Fc regions) of the same origin are linked to a single-chain polypeptide of a different origin to form a dimer or multimer. That is, a dimer or a multimer may be prepared from two or more fragments selected from the group consisting of Fc fragments of IgG Fc, IgA Fc, IgM Fc, IgD Fc, and IgE Fc.

As used herein, the term "hybrid" means that sequences encoding two or more immunoglobulin constant regions of different origins are present in a single-chain of an immunoglobulin constant region (preferably, an Fc region). In the present invention, various hybrid forms are possible. For example, the hybrid domain may be composed of one to four domains selected from the group consisting of CH1, CH2, CH3, and CH4 of IgG Fc, IgM Fc, IgA Fc, IgE Fc, and IgD Fc, and may further include a hinge region.

IgG may be divided into the IgG1, IgG2, IgG3, and IgG4 subclasses, and the present invention may include combinations or hybrids thereof. Preferred are the IgG2 and IgG4 subclasses, and most preferred is the Fc region of IgG4 rarely having effector functions such as complement dependent cytotoxicity (CDC).

The immunoglobulin constant region may have the glycosylated form to the same extent as, or to a greater or lesser extent than the native form or may be the deglycosylated form. Increased or decreased glycosylation or deglycosylation of the immunoglobulin constant region may be achieved by typical methods, for example, by using a chemical method, an enzymatic method or a genetic engineering method using microorganisms. Herein, when deglycosylated, the complement (C1q) binding to an immunoglobulin constant region becomes significantly decreased and antibody-dependent cytotoxicity or complement-dependent cytotoxicity is reduced or removed, thereby not inducing unnecessary immune responses in vivo. In this context, deglycosylated or aglycosylated immunoglobulin constant regions are more consistent with the purpose of drug carriers. Accordingly, the immunoglobulin Fc region may be more specifically an aglycosylated Fc region derived from human IgG4, that is, a human IgG4-derived aglycosylated Fc region. The human-derived Fc region is more preferable than a non-human derived Fc region, which may act as an antigen in the human body and cause undesirable immune responses such as the production of a new antibody against the antigen.

Further, the immunoglobulin constant region of the present invention includes not only the native amino acid sequence but also sequence derivatives (mutants) thereof. The amino acid sequence derivative means that it has an amino acid sequence different from the wild-type amino acid sequence as a result of deletion, insertion, conserved or non-conserved substitution of one or more amino acid residues, or a combination thereof. For instance, amino acid residues at positions 214 to 238, 297 to 299, 318 to 322, or 327 to 331 in IgG Fc, known to be important for linkage, may be used as the sites suitable for modification. Various derivatives, such as those prepared by removing the sites capable of forming disulfide bonds, removing several N-terminal amino acids from native Fc, or adding methionine to the N-terminus of native Fc, may be used. In addition, complement fixation sites, e.g., C1q fixation sites, or ADCC sites may be eliminated to remove the effector function. The techniques of preparing the sequence derivatives of the immunoglobulin constant region are disclosed in International Patent Publication Nos. WO 97/34631 and WO 96/32478.

Amino acid substitutions in a protein or peptide molecule that do not alter the activity of the molecule are well known in the art (H. Neurath, R. L. Hill, The Proteins, Academic Press, New York, 1979). The most common substitutions occur between amino acid residues Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, and Asp/Gly, in both directions. Optionally, amino acids may be modified by phosphorylation, sulfation, acrylation, glycosylation, methylation, farnesylation, acetylation, amidation, or the like.

The above-described immunoglobulin constant region derivative may be a derivative which has a biological activity equivalent to that of the immunoglobulin constant region of the present invention, but has increased structural stability of the immunoglobulin constant region against heat, pH, etc. Further, the immunoglobulin constant region may be obtained from a native type isolated from humans or animals such as cows, goats, pigs, mice, rabbits, hamsters, rats, guinea pigs, etc., or may be their recombinants or derivatives obtained from transformed animal cells or microorganisms. Herein, they may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and F(ab)$_2$ fragments. These fragments may be subjected, for example, to size exclusion chromatography to isolate Fc or pF'c.

Preferably, a human-derived immunoglobulin constant region may be a recombinant immunoglobulin constant region that is obtained from a microorganism.

The protein complex of the present invention may include one or more of a unit structure of a [physiologically active polypeptide/non-peptidyl polymer/immunoglobulin Fc region], in which all components may be linked in a linear form by a covalent bond. The non-peptidyl polymer may have a reactive group at both ends thereof, and is linked to the physiologically active polypeptide and the immunoglobulin Fc region through the reactive group by a covalent bond, respectively. That is, at least one conjugate of the physiologically active polypeptide and the non-peptidyl polymer is linked to one immunoglobulin Fc region by a covalent bond, thereby forming a monomer, dimer, or multimer of the physiologically active polypeptide, which is mediated by the immunoglobulin Fc region. Therefore, an increase in in vivo activity and stability may be more effectively achieved.

The reactive group at both ends of the non-peptidyl polymer is preferably selected from the group consisting of a reactive aldehyde group, a propionaldehyde group, a butyraldehyde group, a maleimide group, and a succinimide derivative. The succinimide derivative may be hydroxy succinimidyl, succinimidyl carboxymethyl, succinimidyl valerate, succinimidyl methylbutanoate, succinimidyl methylpropionate, succinimidyl butanoate, succinimidyl propionate, N-hydroxysuccinimide, or succinimidyl carbonate. In particular, when the non-peptidyl polymer has a reactive aldehyde group at both ends, it is effective in linking of both of the ends with the physiologically active polypeptide and the immunoglobulin with minimal non-specific reactions. A final product generated by reductive alkylation by an aldehyde bond is much more stable than when linked by an amide bond.

The reactive groups at both ends of the non-peptidyl polymer of the present invention may be the same as or different from each other. The non-peptide polymer may possess aldehyde reactive groups at both ends, or it may possess an aldehyde group at one end and a maleimide reactive group at the other end, or an aldehyde group at one end and a succinimide reactive group at the other end, but is not limited thereto.

For example, the non-peptide polymer may possess a maleimide group at one end and an aldehyde group, a propionaldehyde group, or a butyraldehyde group at the other end. Also, the non-peptide polymer may possess a succinimidyl group at one end and an a propionaldehyde group, or a butyraldehyde group at the other end. When a polyethylene glycol having a reactive hydroxy group at both ends thereof is used as the non-peptidyl polymer, the hydroxy group may be activated to various reactive groups by known chemical reactions, or a commercially available polyethylene glycol having a modified reactive group may be used so as to prepare the protein complex of the present invention.

When the physiologically active polypeptide and the immunoglobulin Fc region are linked via the non-peptidyl polymer, each of both of the ends of the non-peptidyl polymer may bind to the N-terminus of the immunoglobulin Fc region and the N-terminus (amino terminus), C-terminus (carboxy terminus), or free reactive group of a lysine residue, a histidine residue, or a cysteine residue of the physiologically active polypeptide.

As used herein, the term "N-terminus" refers to a N-terminus of a peptide, which is a site to which a linker including a non-peptidyl polymer can be conjugated for the purpose of the present invention. Examples of the N-terminus may include not only amino acid residues at the distal end of the N-terminus, but also amino acid residues near the N-terminus, but are not limited thereto. Specifically, the 1st to the 20th amino acid residues from the distal end may be included.

The non-peptidyl polymer of the present invention may be selected from the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, biodegradable polymers such as PLA (polylactic acid) and PLGA (polylactic-glycolic acid), lipid polymers, chitins, hyaluronic acid, and combinations thereof, and specifically, polyethylene glycol, but is not limited thereto. Also, derivatives thereof well known in the art and easily prepared within the skill of the art are included in the non-peptidyl polymer of the present invention. The non-peptidyl polymer may have a molecular weight in the range of 1 kDa to 100 kDa, and specifically 1 kDa to 20 kDa.

The physiologically active polypeptide of the present invention may be exemplified by various physiologically active polypeptides such as hormones, cytokines, interleukins, interleukin-binding proteins, enzymes, antibodies, growth factors, transcription factors, blood factors, vaccines, structural proteins, ligand proteins or receptors, cell surface antigens, receptor antagonists, and derivatives or analogs thereof.

Specifically, the physiologically active polypeptide includes human growth hormones, growth hormone-releasing hormones, growth hormone-releasing peptides, interferons and interferon receptors (e.g., interferon-alpha, -beta, and -gamma, soluble type I interferon receptors), colony-stimulating factors, interleukins (e.g., interleukin-1, -2, -3, -4, -5, -6, -7, -8, -9, -10, -11, -12, -13, -14, -15, -16, -17, -18, -19, -20, -21, -22, -23, -24, -25, -26, -27, -28, -29, -30, etc.) and interleukin receptors (e.g., IL-1 receptor, IL-4 receptor, etc.), enzymes (e.g., glucocerebrosidase, iduronate-2-sulfatase, alpha-galactosidase-A, agalsidase alpha, beta, alpha-L-iduronidase, butyrylcholinesterase, chitinase, glutamate decarboxylase, imiglucerase, lipase, uricase, platelet-activating factor acetylhydrolase, neutral endopeptidase, myeloperoxidase, etc.), interleukin- and cytokine-binding proteins (e.g., IL-18 bp, TNF-binding protein, etc.), macrophage-activating factors, macrophage peptides, B-cell factors, T-cell factors, protein A, allergy inhibitors, cell necrosis glycoproteins, immunotoxins, lymphotoxins, tumor necrosis factor, tumor suppressors, transforming growth factor, alpha-1 anti-trypsin, albumin, alpha-lactalbumin, apolipoprotein-E, erythropoietin, glycosylated erythropoietin, angiopoietins, hemoglobin, thrombin, thrombin receptors activating peptides, thrombomodulin, blood factors VII, VIIa, VIII, IX, and XIII, plasminogen activators, fibrin-binding peptides, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone-stimulating protein, calcitonin, insulin, oxyntomodulin, glucagon, glucagon derivatives, glucagon-like peptides, exendins (Exendin4), atriopeptin, cartilage-inducing factor, elcatonin, connective tissue-activating factor, tissue factor pathway inhibitor, follicle-stimulating hormone, luteinizing hormone, luteinizing hormone-releasing hormone, nerve growth factors (e.g., nerve growth factor, cilliary neurotrophic factor, axogenesis factor-1, brain-natriuretic peptide, glial-derived neurotrophic factor, netrin, neutrophil inhibitor factor, neurotrophic factor, neurturin, etc.), parathyroid hormone, relaxin, secretin, somatomedin, insulin-like growth factor, adrenocortical hormone, glucagon, cholecystokinin, pancreatic polypeptide, gastrin-releasing peptide, corticotrophin-releasing factor, thyroid-stimulating hormone, autotaxin, lactoferrin, myostatin, receptors (e.g., TNFR (P75), TNFR (P55), IL-1 receptor, VEGF receptor, B-cell-activating factor receptor, etc.), receptor antagonists (e.g., IL1-Ra, etc.), cell surface antigens (e.g., CD 2, 3, 4, 5, 7, 11a, 11b, 18, 19, 20, 23, 25, 33, 38, 40, 45, 69, etc.), monoclonal antibodies, polyclonal antibodies, antibody fragments (e.g., scFv, Fab, Fab', F(ab')$_2$, and Fd), and virus-derived vaccine antigens.

Specifically, the physiologically active polypeptide of the present invention may be human growth hormones, interferons (interferon-alpha, -beta, -gamma, etc.) granulocyte colony-stimulating factor, erythropoietin, blood factor VII, blood factor VIIa, blood factor VIII, insulin, oxyntomodulin, glucagon, glucagon-like peptides, exendins, antibody fragments, derivatives thereof, etc. which are frequently administered to the human body for the purpose of treating or preventing a disease. In addition, certain mutants or derivatives are included in the scope of the physiologically active polypeptides of the present invention as long as they have function, structure, activity, or stability substantially identical to or higher than native forms of the physiologically active polypeptides.

In the present invention, the antibody fragment may be Fab, Fab', F(ab')$_2$, Fd, or scFv having an ability to bind to a specific antigen, and preferably, Fab'. The Fab fragments include the variable domain (VL) and constant domain (CL) of the light chain and the variable domain (VH) and the first constant domain (CH1) of the heavy chain. The Fab' fragments differ from the Fab fragments in terms of the addition of several amino acid residues including one or more cysteine residues from the hinge region at the carboxyl terminus of the CH1 domain. The Fd fragments are fragments consisting of only the VH and CH1 domains, and the F(ab')$_2$ fragments are produced by binding of two molecules of Fab' fragments by either disulfide bonding or a chemical reaction. The scFv fragment is a single polypeptide chain, in which only VL and VH domains are linked to each other by a peptide linker.

Further, the protein complex of the present invention may be used in the development of long-acting protein formulations of animal growth hormone such as bovine growth hormone or porcine growth hormone, and long-acting protein formulations for treatment or prevention of animal disease, such as interferon.

Another aspect of the present invention provides a method of preparing the protein complex of the present invention. In particular, the present invention provides a method of preparing a position-specific protein complex, the method comprising: (a) preparing a protein complex by linking at least one non-peptidyl polymer having a reactive group at both ends, at least one physiologically active polypeptide, and at least one immunoglobulin Fc region by a covalent bond, and (b) isolating the protein complex, essentially including the covalently linked physiologically active polypeptide, non-peptidyl polymer, and immunoglobulin Fc region prepared in step (a), in which the non-peptidyl polymer is linked to the N-terminus of the immunoglobulin Fc fragment.

The immunoglobulin Fc region of the present invention may be in the form of a dimer, or in the form of a homodimer or heterodimer. Therefore, the immunoglobulin Fc region constituting the protein complex of the present invention may include one or two or more of a N-terminus. Thus, the immunoglobulin Fc region may be linked to at least one non-peptidyl polymer via the N-terminus. In particular, the immunoglobulin Fc region of the present invention may be in the form of a homodimer, and therefore, linked to one or two non-peptidyl polymers via two N-terminals included in the homodimers of the immunoglobulin Fc region. In this regard, the non-peptidyl polymers may bind to the physiologically active polypeptides, respectively, thereby forming the protein complex.

Accordingly, the protein complex of the present invention may be prepared by linking one or two or more of the non-peptidyl polymer, one or two or more of the physiologically active polypeptide, and one or two or more of the immunoglobulin Fc region via a covalent bond.

In step (a), the covalent bonds between the three components may occur sequentially or at the same time. For example, when the physiologically active polypeptide and the immunoglobulin Fc region are linked to both ends of the non-peptidyl polymer, respectively, any one of the physiologically active polypeptide and the immunoglobulin Fc region may be first linked to one end of the non-peptidyl polymer, and then the other may be linked to the other end of the non-peptidyl polymer. This method is advantageous in that production of by-products other than the desired protein complex is minimized and the protein complex is prepared in high purity.

Therefore, step (a) may comprise:
(i) linking a specific site of the immunoglobulin Fc region or the physiologically active polypeptide to one end of the non-peptidyl polymer via a covalent bond;
(ii) homogeneously isolating a conjugate from the reaction mixture, in which the conjugate is prepared by linking the specific site of the immunoglobulin Fc region or the physiologically active polypeptide to the non-peptidyl polymer; and
(iii) producing a protein complex by linking the physiologically active polypeptide or the specific site of the immunoglobulin Fc region to the other end of the non-peptidyl polymer of the isolated conjugate.

Meanwhile, in the present invention, step (a) includes (a1) preparing a conjugate by linking one end of the non-peptidyl polymer to any one of the immunoglobulin Fc region and the physiologically active polypeptide by a covalent bond; and (a2) isolating the conjugate prepared in step (a1) and linking the other end of the non-peptidyl polymer of the isolated conjugate to the other of the physiologically active polypeptide and the immunoglobulin Fc region by a covalent bond.

Specifically, step (a) may comprise (a1') preparing a conjugate by linking one end of the non-peptidyl polymer to the immunoglobulin Fc region by a covalent bond; and (a2') isolating the conjugate prepared in step (a1') and linking the other end of the non-peptidyl polymer of the isolated conjugate to the physiologically active polypeptide by a covalent bond.

Alternatively, step (a) may include (a1") preparing a conjugate by linking one end of the non-peptidyl polymer to the physiologically active polypeptide by a covalent bond; and (a2") isolating the conjugate prepared in step (a1") and linking the other end of the non-peptidyl polymer of the isolated conjugate to the immunoglobulin Fc region by a covalent bond.

In step (a1), (a1'), or (a1") of the present invention, the reaction mole ratio between the physiologically active polypeptide and the non-peptidyl polymer may be in the range from 1:1 to 1:30, and the reaction mole ratio between the immunoglobulin Fc region and the non-peptidyl polymer may be in the range from 1:1 to 1:20. Specifically, in step (a1'), the reaction mole ratio between the immunoglobulin Fc region and the non-peptidyl polymer may be in the range from 1:1 to 1:20, and in particular, in the range from 1:1 to 1:15, 1:1 to 1:10, or 1:1 to 1:4. In step (a1"), the reaction mole ratio between the physiologically active polypeptide and the non-peptidyl polymer may be in the range from 1:1 to 1:30, and in particular, in the range from 1:1 to 1:15 or 1:1 to 1:10. A preparation yield and cost may be optimized depending on the reaction mole ratio.

In the present invention, step (a1), (a1'), or (a1") may be performed in a pH condition from 4.0 to 9.0; step (a1), (a1'), or (a1") may be performed at a temperature from 4.0° C. to 25° C.; in step (a1), (a1'), or (a1"), the reaction concentration of the immunoglobulin Fc region or physiologically active polypeptide may be in the range from 0.1 mg/mL to 100 mg/mL.

In step (a2), (a2'), or (a2") of the present invention, the reaction mole ratio between the conjugate and the immunoglobulin Fc region or the physiologically active polypeptide may be in the range from 1:0.1 to 1:20, and in particular, in the range from 1:0.2 to 1:10. Specifically, in step (a2'), the reaction mole ratio between the conjugate and the physiologically active polypeptide may be in the range from 1:0.1 to 1:20, and in step (a2"), the reaction mole ratio between the conjugate and the immunoglobulin Fc region may be in the range from 1:0.1 to 1:20. A preparation yield and cost may be optimized depending on the reaction mole ratio.

In the present invention, step (a2), (a2'), or (a2") may be performed in a pH condition from 4.0 to 9.0; step (a2), (a2'), or (a2") may be performed at a temperature from 4.0° C. to 25° C.; in step (a2), (a2'), or (a2"), the reaction concentration of the immunoglobulin Fc region or physiologically active polypeptide may be in the range from 0.1 mg/mL to 100 mg/mL.

Meanwhile, the preparation method of the present invention may be a method of preparing a position-specific protein complex, including (a') preparing a conjugate by linking one end of the non-peptidyl polymer to any one of the immunoglobulin Fc region and the physiologically active polypeptide by a covalent bond, in which the reaction mole ratio between the physiologically active polypeptide and the non-peptidyl polymer is in the range from 1:1 to 1:30, the reaction mole ratio between the immunoglobulin Fc region and the non-peptidyl polymer is in the range from 1:1 to 1:20, a reducing agent is contained in the range from 1 mM to 100 mM, the reaction is performed in the condition of pH from 4.0 to 9.0, at a temperature from 4.0° C. to 25° C., and the reaction concentration of the immunoglobulin Fc region or physiologically active polypeptide is in the range from 0.1 mg/mL to 100 mg/mL;

(b') isolating the conjugate prepared in step (a') and linking the other end of the non-peptidyl polymer of the isolated conjugate to the other of the immunoglobulin Fc region and the physiologically active polypeptide by a covalent bond, in which the reaction mole ratio between the conjugate and the immunoglobulin Fc region or the physiologically active polypeptide is in the range from 1:0.1 to 1:20, a reducing agent is contained in the range from 1 mM to 100 mM, the reaction is performed in the condition of pH from 4.0 to 9.0, at a temperature from 0° C. to 25° C., and the concentration of the immunoglobulin Fc region or physiologically active polypeptide is in the range from 0.1 mg/mL to 100 mg/mL; and (c') isolating the protein complex, essentially including the covalently linked physiologically active polypeptide, non-peptidyl polymer, and immunoglobulin Fc region prepared in step (b'), in which the non-peptidyl polymer is linked to the N-terminus of the immunoglobulin Fc fragment, but is not limited thereto.

The reactions in step (a1), step (a1'), step (a1"), step (a2), step (a2'), and step (a2") of the present invention may be performed in the presence of a reducing agent, considering the type of the reactive groups at both ends of the non-peptidyl polymer which participate in the reactions, if necessary. The reducing agent of the present invention may be sodium cyanoborohydride (NaCNBH$_3$), sodium borohydride, dimethylamine borate, or pyridine borate. In this regard, a concentration of the reducing agent (e.g., sodium cyanoborohydride), temperature and pH of a reaction solution, and total concentrations of the physiologically active polypeptide and the immunoglobulin Fc region participating in the reaction are important in terms of production yield and purity. To maximize the production of a high-purity homogeneous complex, various combinations of the conditions are needed. According to the feature of the physiologically active polypeptide to be prepared, various conditions are possible, but not limited to, the reducing agent (e.g., sodium cyanoborohydride) may be contained in the range from 1 mM to 100 mM, the reaction solution may be at a temperature from 0° C. to 25° C. and in the condition of pH from 4.0 to 9.0, and the concentration of the reaction protein (concentration of the immunoglobulin Fc region or physiologically active polypeptide included upon the reaction) may be in the range from 5 mg/mL to 100 mg/mL.

Meanwhile, the separation of the conjugate in step (a2), step (a2'), and step (a2") may be performed, if necessary, by a method selected from general methods which are used in protein separation, considering the properties such as purity, hydrophobicity, molecular weight, and electrical charge which are required for the separated conjugate. For example, the separation may be performed by applying various known methods, including size exclusion chromatography, affinity chromatography, hydrophobic chromatography, or ion exchange chromatography, and if necessary, a plurality of different methods are used in combination to purify the conjugate with a higher purity.

According to the features of the physiologically active polypeptide to be prepared, various conditions are possible. However, in order to separate the immunoglobulin Fc region or the physiologically active polypeptide conjugate linked to the non-peptidyl polymer, size exclusion chromatography is generally performed. For further scale-up and separation of isomers generated by binding of the non-peptidyl polymer at a position other than the desired position or a small amount of denatured forms generated during preparation, affinity chromatography, hydrophobic chromatography, or ion exchange chromatography may be also used.

In the present invention, step (b) may be performed, if necessary, by a method selected from general methods which are used in protein separation, considering the properties such as hydrophobicity, molecular weight, and electrical charge, in order to finally purify a high-purity complex. For example, the separation may be performed by applying various known methods, including size exclusion chromatography, affinity chromatography, hydrophobic chromatography, or ion exchange chromatography, and if necessary, a plurality of different methods are used in combination to purify the complex with a higher purity. According to the features of the desired complex consisting of the physiologically active polypeptide, the non-peptidyl polymer, and the Fc constant region, various separation conditions are possible. However, in order to separate the complex in which the physiologically active polypeptide and the immunoglobulin Fc region are respectively linked to both ends of the non-peptidyl polymer, size exclusion chromatography is generally performed. For further scale-up and effective separation of isomers or side-reaction products generated by binding of the physiologically active polypeptide or the immunoglobulin Fc region, and non-peptidyl polymer at a position other than the desired position, or a small amount of denatured forms generated during preparation, unreacted physiologically active polypeptide, non-peptidyl polymer, and immunoglobulin Fc region, hydrophobic chromatography, ion exchange chromatography, or affinity chromatography may be used in combination. In particular, hydrophobic chromatography and ion exchange chromatography may be used in combination, and a plurality of hydrophobic chromatography or a plurality of ion exchange chromatography is also possible. According to the complex to be prepared, ion exchange chromatography or hydrophobic chromatography may be used singly.

In the present invention, the ion exchange chromatography is to separate a protein by passing charged protein at a specific pH through a charged ion resin-immobilized chromatography column and separating the protein by a difference in the migration rate of the protein, and it may be anion exchange chromatography or cation exchange chromatography.

The anion exchange chromatography is to use a cation resin, and a functional group of the resin constituting the corresponding anion exchange chromatography may be any one selected from the group consisting of quaternary ammonium (Q), quaternary aminoethyl (QAE), diethylaminoethyl (DEAE), polyethylene amine (PEI), dimethylaminomethyl (DMAE), and trimethylaminoethyl (TMAE), but is not limited thereto.

Further, the cation exchange chromatography is to use an anion resin, and a functional group of the resin constituting the corresponding cation exchange chromatography may be any one selected from the group consisting of methylsulfonate (S), sulfopropyl (SP), carboxymethyl (CM), sulfoethyl (SE), and polyaspartic acid, but is not limited thereto.

In the present invention, a functional group of the resin constituting the hydrophobic chromatography may be any one selected from the group consisting of phenyl, octyl, (iso)propyl, butyl, and ethyl, but is not limited thereto.

In the present invention, a functional group of the resin constituting the size exclusion chromatography may be any one selected from the group consisting of superdex, sephacryl, superpose, and sephadex, but is not limited thereto.

Furthermore, the affinity chromatography in the present invention is to separate a protein by a difference in the migration rate of the protein, which is caused by interaction between the protein and a ligand capable of interacting with the protein in a resin onto which the ligand is immobilized. A functional group of the resin constituting the affinity chromatography may be any one selected from the group consisting of protein A, heparin, blue, benzamidine, metal ions (cobalt, nickel, and copper), and an antibody to a part or the entirety of the constituting components of the protein complex, in which both ends of the non-peptidyl polymer are respectively conjugated to the immunoglobulin Fc region and the physiologically active polypeptide, but is not limited thereto.

In the present invention, step (b) is to isolate the protein complex in which the non-peptidyl polymer and the immunoglobulin Fc region are linked to each other via the N-terminus of the immunoglobulin Fc region.

Still another aspect of the present invention provides a method for preparing a protein complex with N-terminal selectivity of 90% or higher. Specifically, the protein complex prepared by the method of the present invention may be one, in which one end of the non-peptidyl polymer may be linked to the N-terminus of the immunoglobulin Fc region with N-terminal selectivity of 90% or higher, more specifically 95% or higher, even more specifically 98% or higher, and yet even more specifically 99% or higher, but is not limited thereto.

As used herein, the term "linking with N-terminal selectivity of 90% or higher" means that, in 90% or more of the protein complex prepared by purification of the protein complex fractions obtained by a series of reactions according to the present invention, the non-peptidyl polymer is linked to the N-terminus of the Fc region in a position-specific manner. As used herein, the term "90% or higher" may refer to v/v, w/w, and peak/peak, but is not limited to a particular unit. The yield of the protein complex comprising the non-peptidyl polymer linked to the N-terminus of the Fc region in a position-specific manner may vary by reaction conditions, a reactor of the non-peptidyl polymer, etc.

In Examples of the present invention, it was confirmed that a protein complex with N-terminal selectivity of 90% or higher can be prepared by the method according to the present invention, via preparation of various physiologically active polypeptides, non-peptidyl polymers, and Fc complexes.

Still another aspect of the present invention provides a pharmaceutical composition for improving in vivo duration and stability of the physiologically active polypeptide, the composition including the protein complex or a protein complex prepared by the preparation method as an active ingredient.

Specifically, the pharmaceutical composition may comprise a protein complex, which includes the physiologically active polypeptide-non-peptidyl polymer-N-terminus of an immunoglobulin Fc region, in an amount of 90% or higher, more specifically 95% or higher, even more specifically 98% or higher, and yet even more specifically 99% or higher, but is not limited thereto. As used herein, the term "90% or higher" may refer to v/v, w/w, and peak/peak, but is not limited to a particular unit.

The pharmaceutical composition may further include a pharmaceutically acceptable excipient.

The pharmaceutical composition of the present invention may be administered via various routes including oral, percutaneous, subcutaneous, intravenous, and intramuscular routes, preferably, in the form of an injectable formulation. Further, the pharmaceutical composition of the present invention may be formulated by a method known in the art in order to provide rapid, long-lasting, or delayed release of the active ingredient after administration thereof to a mammal. The formulation may be a tablet, a pill, a powder, a sachet, an elixir, a suspension, an emulsion, a solution, a syrup, an aerosol, a soft or hard gelatin capsule, a sterile injectable solution, or a sterile powder. Examples of suitable carriers, excipients, and diluents may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil. The pharmaceutical composition may further include a filler, an anticoagulant, a lubricant, a wetting agent, a flavoring agent, an emulsifying agent, a preservative, etc.

A practical administration dose of the protein complex of the present invention may be determined by several related factors including the types of diseases to be treated, administration routes, the patient's age, gender, weight, and severity of the illness, as well as by the types of the physiologically active polypeptide as an active component. Since the protein complex of the present invention has excellent blood duration and in vivo potency, it can remarkably reduce the administration dose and frequency of a peptide drug including the protein complex of the present invention.

Still another aspect of the present invention provides a population of protein complexes including the protein complex prepared according to the above method in an amount of 90% or higher.

As used herein, the terms "population of complex", and "population" may be used interchangeably, and they refer to a group of protein complexes including protein complexes, in which a non-peptidyl polymer is linked to the N-terminus of an Fc region, and/or protein complexes, in which a non-peptidyl polymer is linked to a region other than the N-terminus of an Fc region.

The population may include only the protein complexes, in which a non-peptidyl polymer is linked to the N-terminus of an Fc region, or the protein complexes, in which a non-peptidyl polymer is linked to a region other than the N-terminus of an Fc region. Specifically, the percentage of the protein complexes, in which a non-peptidyl polymer is linked to a region other than the N-terminus of an Fc region, included in the population may be 90% or higher, more specifically 95% or higher, even more specifically 98% or higher, and yet even more specifically 99% or higher, but is not limited thereto. As used herein, the term "90% or higher" may refer to v/v, w/w, and peak/peak, but is not limited to a particular unit.

For the purpose of the present invention, the population may refer to a population with an increased percentage of the protein complexes, in which a non-peptidyl polymer is linked to a region other than the N-terminus of an Fc region, by removing impurities, unreacted materials, etc., from the protein complexes prepared thereof. Additionally, the population may refer to one which was prepared by a method for preparing protein complexes with N-terminal selectivity of 90% or higher, but is not limited thereto. The population may be efficiently purified by the method of the present invention.

MODE FOR INVENTION

Hereinafter, the present invention will be described in more detail with reference to Examples. However, these Examples are for illustrative purposes only, and the invention is not intended to be limited by these Examples.

Example 1: Preparation of Complex of Interferon Alpha (IFNα)-PEG-N-Terminus Region of Immunoglobulin Fc 1-1. Preparation of IFNα-PEG Conjugate ALD-PEG-ALD (IDB, Korea), which is polyethylene glycol (PEG) having a molecular weight of 3.4 kDa and aldehyde reactive groups at both ends thereof, was added to 5 mg/mL of human interferon alpha-2b (hIFNα-2b, molecular weight: 19 kDa) dissolved in 100 mM phosphate buffer at a molar ratio of hIFNα:PEG of 1:5 to 1:10. A reducing agent, sodium cyanoborohydride (NaCNBH$_3$, Sigma) was added thereto at a final concentration of 20 mM, and allowed to react at 4° C. to 8° C. under slow stirring for about 1 hour. To obtain a conjugate in which PEG is selectively linked to the amino terminus of interferon alpha and PEG and interferon alpha are linked to each other at a ratio of 1:1, the reaction mixture was subjected to SP HP (GE healthcare, USA) anion exchange chromatography to purify an IFNα-PEG conjugate with high purity.

1-2. Preparation of IFNα-PEG-Fc Complex

In order to link the IFNα-PEG conjugate purified in Example 1-1 to the N-terminal proline residue of immunoglobulin Fc, the immunoglobulin Fc fragment was added and reacted at a molar ratio of IFNα-PEG conjugate:immunoglobulin Fc of 1:1 to 1:4. The reaction solution was prepared as 100 mM phosphate buffer (pH 5.5 to 6.5), and sodium cyanoborohydride (NaCNBH$_3$, Sigma) was added as a reducing agent at a final concentration of 20 mM to 50 mM. The reaction was allowed at 4° C. to 8° C. for about 12 hours to 16 hours under slow stirring.

1-3. Isolation and Purification of IFNα-PEG-Fc Complex

In order to remove unreacted materials and by-products after the binding reaction of Example 1-2 and to purify the IFNα-PEG-Fc protein complex thus produced, the reaction mixture was buffer-exchanged to 10 mM Tris (pH 7.5), and then passed through a Source Q (GE healthcare, USA) anion exchange chromatography column to remove unreacted Fc and to obtain an IFNα-PEG-Fc protein complex fraction. In detail, the reaction solution was applied to Source Q column equilibrated with 10 mM Tris (pH 7.5), and the column was subjected to isocratic solvent washing using 20 mM Tris (pH 7.5) buffer solution containing 50 mM sodium chloride (NaCl) to remove impurities. Then, the IFNα-PEG-Fc protein complex was eluted with a concentration gradient of a buffer solution containing 150 mM sodium chloride (NaCl). A small amount of unreacted Fc and interferon alpha dimer were present as impurities in the obtained IFNα-PEG-Fc protein complex fraction. In order to remove the impurities, Source iso (GE healthcare, USA) hydrophobic chromatography was further performed. In detail, Source iso (GE healthcare, USA) was equilibrated with a 20 mM potassium phosphate (pH 6.0) buffer solution containing about 1.3 M ammonium sulfate, and then the purified IFNα-PEG-Fc protein complex fraction was applied thereto. Finally, a high-purity IFNα-PEG-Fc protein complex was purified with a linear concentration gradient of a 20 mM potassium phosphate (pH 6.0) buffer solution. N-terminal selectivity of the Fc region of the prepared IFNα-PEG-Fc protein complex was examined by peptide mapping, and the selectivity was found to be 90% or higher.

Example 2: Preparation of Human Growth Hormone (hGH)-PEG-Fc Complex 2-1. Preparation of hGH-PEG Conjugate ALD-PEG-ALD (IDB, Korea), which is polyethylene glycol (PEG) having a molecular weight of 3.4 kDa and aldehyde reactive groups at both ends thereof, was added to 5 mg/mL of human growth hormone (hGH, molecular weight: 22 kDa) dissolved in 100 mM phosphate buffer at a molar ratio of hGH:PEG of 1:5 to 1:10. A reducing agent, sodium cyanoborohydride (NaCNBH$_3$, Sigma) was added thereto at a final concentration of 20 mM, and allowed to react at 4° C. to 8° C. under slow stirring for about 1 hour. To obtain a conjugate in which PEG is selectively linked to the amino terminus of human growth hormone and PEG and hGH are linked to each other at a ratio of 1:1, the reaction mixture was subjected to Source Q (GE healthcare, USA) anion exchange chromatography to purify hGH-PEG with high purity.

2-2. Preparation of hGH-PEG-Fc Complex

In order to link the hGH-PEG conjugate purified in Example 2-1 to the N-terminus of immunoglobulin Fc, the immunoglobulin Fc fragment was added to a molar ratio of hGH-PEG conjugate:immunoglobulin Fc of 1:1 to 1:4 and reacted. The reaction solution was prepared as 100 mM phosphate buffer (pH 5.5 to 6.5), and sodium cyanoborohydride (NaCNBH$_3$, Sigma) was added as a reducing agent at a final concentration of 20 mM. The reaction was allowed at 4° C. to 8° C. under slow stirring.

2-3. Isolation and Purification of hGH-PEG-Fc Complex

In order to remove unreacted materials and by-products after the binding reaction of Example 2-2 and to purify the hGH-PEG-Fc protein thus produced, the reaction mixture was buffer-exchanged to 10 mM Tris (pH 7.5), and then passed through a Source Q (GE healthcare, USA) anion exchange chromatography column to remove unreacted Fc and to obtain an hGH-PEG-Fc protein complex fraction. In detail, the reaction solution was applied to a Source Q column equilibrated with 10 mM Tris (pH 7.5), and the column was subjected to isocratic solvent washing using a 20 mM Tris (pH 7.5) buffer solution containing 70 mM sodium chloride (NaCl) to remove impurities. Then, the high-purity hGH-PEG-Fc protein complex was eluted with a concentration gradient of a 20 mM Tris (pH 7.5) buffer solution containing 150 mM sodium chloride. N-terminal selectivity of the Fc region of the prepared hGH-PEG-Fc protein complex was examined by peptide mapping, and the selectivity was found to be 90% or higher.

Example 3: Preparation of Human Granulocyte Colony Stimulating Factor (G-CSF)-PEG-Fc Complex $^{17,65}$S-G-CSF-PEG-Fc protein complex was prepared using a derivative ($^{17,65}$S-G-CSF) prepared by substituting serine for the amino acids at positions 17 and 65 of the native G-CSF, and then purified.

3-1. Preparation of $^{17,65}$S-G-CSF-PEG Conjugate

ALD-PEG-ALD (IDB, Korea), which is polyethylene glycol (PEG) having a molecular weight of 3.4 kDa and aldehyde reactive groups at both ends thereof, was added to 5 mg/mL of $^{17,65}$S-G-CSF (molecular weight: 18 kDa) dissolved in 100 mM phosphate buffer at a molar ratio of G-CSF:PEG of 1:5 to 1:10. A reducing agent, sodium cyanoborohydride (NaCNBH$_3$, Sigma), was added thereto at a final concentration of 20 mM, and allowed to react at 4° C. to 8° C. under slow stirring for about 1 hour. To obtain a conjugate in which PEG is selectively linked to the amino terminus of human granulocyte colony stimulating factor and PEG and G-CSF are linked to each other at a ratio of 1:1, the reaction mixture was subjected to SP HP (GE healthcare, USA) cation exchange chromatography to purify a $^{17,65}$S-G-CSF-PEG conjugate with a high purity.

3-2. Preparation of $^{17,65}$S-G-CSF-PEG-Fc Complex

In order to link the $^{17,65}$S-G-CSF-PEG conjugate purified in Example 3-1 to the N-terminus of immunoglobulin Fc, the immunoglobulin Fc fragment was added and reacted at a molar ratio of $^{17,65}$S-G-CSF-PEG conjugate:immunoglobulin Fc of 1:1 to 1:4. The reaction solution was prepared as 100 mM phosphate buffer (pH 5.5 to 6.5), and sodium cyanoborohydride (NaCNBH$_3$, Sigma) was added as a reducing agent at a final concentration of 20 mM. The reaction was allowed at 4° C. to 8° C. under slow stirring.

3-3. Isolation and Purification of $^{17,65}$S-G-CSF-PEG-Fc Complex

In order to remove unreacted materials and by-products after the binding reaction of Example 3-2 and to purify the $^{17,65}$S-G-CSF-PEG-Fc protein complex thus produced, the reaction mixture was buffer-exchanged to 10 mM Tris (pH 8.0) containing 2 M NaCl, and then passed through a Source Phenyl column. To remove impurities, the $^{17,65}$S-G-CSF-PEG-Fc protein complex was purified with a concentration gradient of 20 mM Tris (pH 8.0) buffer solution. A small amount of unreacted immunoglobulin Fc and $^{17,65}$S-G-CSF dimer as impurities were present in the obtained $^{17,65}$S-G-CSF-PEG-Fc protein complex fraction. In order to remove the impurities, Q HP (GE healthcare, USA) anion chromatography was further performed. Q HP (GE healthcare, USA) was equilibrated with a 20 mM Tris (pH 8.0) buffer solution, and then the purified $^{17,65}$S-G-CSF-PEG-Fc protein complex fraction was applied thereto. Finally, a high-purity $^{17,65}$S-G-CSF-PEG-Fc protein complex was purified with a linear concentration gradient of a 20 mM Tris (pH 8.0) buffer solution containing 1 M sodium chloride. N-terminal selectivity of the Fc region of the prepared $^{17,65}$S-G-CSF-PEG-Fc protein complex was examined by peptide mapping, and the selectivity was found to be 90% or higher.

Example 4: Preparation of Human Erythropoietin (EPO)-PEG-Fc Complex

4-1. Preparation of Human Erythropoietin (EPO)-PEG Conjugate

ALD-PEG-ALD (IDB, Korea), which is polyethylene glycol (PEG) having a molecular weight of 3.4 kDa and aldehyde reactive groups at both ends thereof, was added to 5 mg/mL of human erythropoietin (EPO, molecular weight: 30.6 kDa) dissolved in 100 mM phosphate buffer at a molar ratio of EPO:PEG of 1:15. A reducing agent, sodium cyanoborohydride (NaCNBH$_3$, Sigma), was added thereto at a final concentration of 20 mM, and allowed to react at 4° C. to 8° C. under slow stirring for about 2 hours. To obtain a conjugate in which PEG is selectively linked to the amino terminus of human erythropoietin and PEG and human erythropoietin are linked to each other at a ratio of 1:1, the reaction mixture was subjected to SP HP (GE healthcare, USA) cation exchange chromatography to elute a main fraction containing EPO-PEG.

4-2. Preparation of EPO-PEG-Fc Complex

In order to link the EPO-PEG conjugate purified in Example 4-1 to the N-terminus of immunoglobulin Fc, the immunoglobulin Fc fragment was added and reacted at a molar ratio of EPO-PEG conjugate:Fc of 1:4. The reaction solution was prepared as 100 mM phosphate buffer (pH 5.5 to 6.5), and sodium cyanoborohydride (NaCNBH$_3$, Sigma) was added as a reducing agent at a final concentration of 20 mM. The reaction was allowed at 4° C. to 8° C. under slow stirring for about 12 hours to 16 hours.

4-3. Isolation and Purification of EPO-PEG Fc Complex

In order to remove unreacted materials and by-products after the binding reaction of Example 4-2 and to purify the EPO-PEG-Fc protein complex thus produced, the reaction mixture was passed through a Source Q (GE healthcare, USA) anion exchange chromatography column to remove unreacted Fc and to obtain an EPO-PEG-Fc protein complex fraction. The reaction mixture was applied to a Source Q column equilibrated with 20 mM Tris (pH 7.5) buffer. The EPO-PEG-Fc protein complex was purified with a concentration gradient of a buffer solution containing 1 M sodium chloride (NaCl). A small amount of unreacted immunoglobulin Fc and EPO dimer as impurities was present in the obtained EPO-PEG-Fc protein complex fraction. In order to remove the impurities, Source iso (GE healthcare, USA) hydrophobic chromatography was further performed. In detail, Source iso (GE healthcare, USA) was equilibrated with a 50 mM Tris (pH 7.5) buffer solution containing 1.6 M ammonium sulfate, and then the purified EPO-PEG-Fc protein complex fraction was applied thereto. Finally, a high-purity EPO-PEG-Fc protein complex was purified with a linear concentration gradient of a 50 mM Tris (pH 7.5) buffer solution. N-terminal selectivity of the Fc region of the prepared EPO-PEG-Fc protein complex was examined by peptide mapping, and the selectivity was found to be 90% or higher.

Example 5: Preparation of Human Insulin-PEG-Fc Complex

5-1. Preparation of Insulin-PEG Conjugate

Insulin powder was dissolved in 10 mM HCl, and then reacted with 3.4 K propion-ALD$_2$ PEG (PEG having two propionaldehyde groups, IDB, Korea) at room temperature for about 2 hours at a molar ratio of insulin:PEG of 1:2 and an insulin concentration of 5 mg/mL to pegylate the N-terminus of the insulin beta chain. This reaction was conducted in 50 mM sodium citrate at pH 6.0 and 45% isopropanol, and 2 mM to 20 mM of sodium cyanoborohydride (NaCNBH3, Sigma) was added thereto. The reaction solution was purified with an SP HP (GE Healthcare) column using a buffer containing sodium citrate (pH 3.0) and 45% EtOH, and a KCl concentration gradient.

5-2. Preparation of Insulin-PEG-Fc Complex

In order to prepare an insulin-PEG-Fc complex, the mono-PEGylated insulin prepared in Example 5-1 and Fc were reacted at a molar ratio of about 1:1 with a total protein level of 20 mg/mL to 50 mg/mL at 20° C. to 25° C. for about 15 hours to 17 hours. In this regard, the reaction solution was 100 mM HEPES, 22 mM potassium phosphate, and 10% ethanol at pH 7.5 to 8.5, and a reducing agent, 20 mM sodium cyanoborohydride (NaCNBH$_3$, Sigma), was added thereto.

5-3. Isolation and Purification of Insulin-PEG-Fc Complex

After completion of the reaction, the reaction solution was passed through a Source Q (GE Healthcare) column to isolate and purify the unreacted insulin, the unreacted immunoglobulin Fc fragment, the insulin-PEG-Fc complex, and the complex in which two or more mono-PEGylated insulin (insulin-PEG) are coupled using Tris-HCl (pH 7.5) buffer and a NaCl concentration gradient. In this regard, a preparation ratio of the insulin-PEG-immunoglobulin Fc fragment complex was determined by examining UV absorbance of purification chromatography at 280 nm.

Then, Source iso (GE Healthcare) was used as a secondary column to remove any residual immunoglobulin Fc and a multi-pegylated insulin complex. In this case, the elution was conducted using a concentration gradient of ammonium sulfate containing Tris-HCl (pH 7.5) to purify a high-purity insulin-PEG-Fc complex. N-terminal selectivity of the Fc region of the insulin-PEG-Fc complex thus prepared was examined by peptide mapping, and the selectivity was found to be 90% or higher.

Example 6: Preparation of Exendin4 Derivative (CA-Exendin 4)-PEG-Fc Complex 6-1. Preparation of CA-Exendin4 Conjugate Insulin powder was dissolved in 10 mM HCl, and then reacted with 3.4 K propion-ALD$_2$ PEG (PEG having two propionaldehyde groups, IDB, Korea) at 4° C. to 8° C. to room temperature for about 4 hours to 12 hours at a molar ratio of CA-Exendin4:PEG of 1:5 to 1:15 and a CA-Exendin4 concentration of 6 mg/mL to 12 mg/mL to pegylate the lysine residue of CA-Exendin4. This reaction was conducted in 0.1 M HEPES at pH 7.5 to 8.5 and 45% isopropanol, and 2 mM to 20 mM of sodium cyanoborohydride (NaCNBH$_3$, Sigma) was added thereto. The reaction solution was purified with a Source S (GE Healthcare) column using buffer containing sodium citrate (pH 2.0) and 45% EtOH, and a KCl concentration gradient.

6-2. Preparation of CA-Exendin4-PEG-Fc Complex

In order to prepare a CA-Exendin4-PEG-Fc complex, the mono-PEGylated CA-Exendin4 prepared in Example 6-1 and Fc were reacted at a total protein level of 10 mg/mL to 50 mg/mL at 4° C. to 8° C. for about 12 hours to 17 hours. In this regard, the reaction solution was 0.1 M potassium phosphate at pH 5.5 to 8.5, and a reducing agent, 20 mM sodium cyanoborohydride (NaCNBH$_3$, Sigma), was added thereto.

6-3. Isolation and Purification of CA-Exendin4-PEG-Fc Complex

After completion of the reaction, the reaction solution was passed through a Source Phenyl (GE Healthcare) column to isolate and purify the unreacted immunoglobulin Fc fragment using Tris-HCl (pH 7.5) buffer and a NaCl concentration gradient. In this regard, a preparation ratio of the CA-Exendin4-PEG-immunoglobulin Fc fragment complex was determined by examining UV absorbance of purification chromatography at 280 nm.

Then, Source Q (GE Healthcare) was used as a secondary column to remove any residual immunoglobulin Fc and multi-pegylated CA-Exendin4 complex. In this case, the elution was conducted using a concentration gradient of NaCl containing Tris-HCl (pH 7.5) to purify a high-purity CA-Exendin4-PEG-Fc complex. N-terminal selectivity of the Fc region of the CA-Exendin4-PEG-Fc complex thus prepared was examined by peptide mapping, and the selectivity was found to be 90% or higher.

Example 7: Preparation of Protein Complex Using PEG with Different Reactive Groups 7-1. Preparation of $^{17,65}$S-G-CSF-PEG Conjugate SMB-PEG-SMB (Nektar, USA), which is polyethylene glycol (PEG) having a molecular weight of 3.4 kDa and succinimidyl alpha-methylbutanoate (SMB) reactive groups at both ends thereof, was added to 10 mg/mL of $^{17,65}$S-G-CSF (molecular weight 18 kDa) dissolved in 20 mM phosphate buffer (pH 8.0) at a molar ratio of G-CSF:PEG of 1:3, and allowed to react at room temperature under slow stirring for about 30 minutes. To obtain a conjugate in which PEG is selectively linked to the amino terminus of $^{17,65}$S-G-CSF and PEG and $^{17,65}$S-G-CSF are linked to each other at a ratio of 1:1, the reaction mixture was subjected to SP HP (GE healthcare, USA) cation exchange chromatography.

7-2. Preparation of $^{17,65}$S-G-CSF-PEG-Fc Complex

In order to link the $^{17,65}$S-G-CSF-PEG conjugate purified in Example 7-1 to a region other than the N-terminus of immunoglobulin Fc, the immunoglobulin Fc fragment was added and reacted at a molar ratio of $^{17,65}$S-G-CSF-PEG conjugate:immunoglobulin Fc of 1:4 to 1:8. The reaction was allowed in 20 mM phosphate buffer (pH 5.5 to 6.5) at room temperature for about 2 hours under slow stirring.

7-3. Isolation and Purification of $^{17,65}$S-G-CSF-PEG-Fc Complex

In order to remove unreacted materials and by-products after the binding reaction of Example 7-2 and to purify the $^{17,65}$S-G-CSF-PEG-Fc protein complex thus produced, the reaction mixture was passed through a Q HP (GE Healthcare, USA) anion exchange chromatography column and thus unbound Fc was removed and a $^{17,65}$S-G-CSF-PEG-Fc protein complex fraction was obtained. The reaction solution was applied to a Q HP column equilibrated with 20 mM Tris (pH 8.0) buffer, and the $^{17,65}$S-G-CSF-PEG-Fc protein complex was purified with a concentration gradient of a buffer solution containing 1 M sodium chloride (NaCl). A small amount of unreacted immunoglobulin Fc and $^{17,65}$S-G-CSF dimer as impurities was present in the obtained $^{17,65}$S-G-CSF-PEG-Fc protein complex fraction. In order to remove the impurities, Source iso (GE Healthcare, USA) hydrophobic chromatography was further performed. Finally, a high-purity $^{17,65}$S-G-CSF-PEG-Fc protein complex was purified with a linear concentration gradient of 50 mM Tris (pH 7.5) buffer solution containing 1.2 M ammonium sulfate using Source iso (GE Healthcare, USA). N-terminal selectivity of the Fc region of the prepared $^{17,65}$S-G-CSF-PEG-Fc protein complex was examined by peptide mapping, and the selectivity was found to be 90% or higher.

Example 8: Preparation of Protein Complex Using PEG with Different Reactive Groups A FacVII-ATKAVC-PEG-Fc complex was prepared using FacVII-ATKAVC, which is a FacVII derivative of Korean Patent Application No. 10-2012-0111537 previously submitted by the present inventors.

8-1. Isolation and Purification of PEG-Fc Complex

First, to link an aldehyde reactive group of maleimide-10 kDa-PEG-aldehyde (NOF, Japan) to the N-terminus of immunoglobulin Fc fragment, the immunoglobulin Fc region and maleimide-10 kDa PEG-aldehyde were mixed at a molar ratio of 1:1 in a 100 mM phosphate buffer solution (pH 5.5 to 6.5), and a reducing agent, 20 mM sodium cyanoborohydride (NaCNBH$_3$, Sigma), was added thereto under a protein concentration of 10 mg/mL. The reaction was allowed at a low temperature (4° C. to 8° C.) for about 2 hours. To obtain a monoPEGylated immunoglobulin Fc fragment (maleimide-10 kDa PEG-Fc), Source Q (GE Healthcare, USA) anion chromatography was performed, and elution was performed with a concentration gradient of sodium chloride in 20 mM Tris buffer at pH 7.5.

8-2. Preparation of FacVII-ATKAVC-PEG-Fc Complex

FacVII-ATKAVC was reacted in 10 mM glycylglycine buffer at pH 5.5 at room temperature for about 2 hours by adding 0.5 mM to 2 mM triphenylphosphine-3,3',3"-trisulfonic trisodium salt hydrate as a reducing agent so as to reduce the C-terminus. The C-terminus-reduced FacVII-ATKAVC and monoPEGylated immunoglobulin Fc fragment (maleimide-10 kDa PEG-Fc) were mixed at a molar ratio of 1:4 to 1:20, and reaction was allowed at a total protein concentration of 1 mg/mL to 2 mg/mL in 50 mM Tris buffer at pH 7.5 at room temperature for about 2 hours.

8-3. Isolation and Purification of FacVII-ATKAVC-PEG-Fc Complex

The reaction solution of Example 8-2 was subjected to Source Q anion chromatography, and the FacVII-ATKAVC-10 kDa PEG-Fc complex was eluted with a concentration gradient of sodium chloride in a 20 mM Tris buffer solution at pH 7.5. To activate FacVII of the FacVII-ATKAVC-PEG-Fc complex, reaction was allowed in a 0.1 M Tris-HCl buffer solution at pH 8.0 under conditions of about 4 mg/mL of FacVII for about 18 hours at a low temperature (4° C. to 8° C.). Finally, high-purity FacVIIa-ATKAVC-PEG-Fc was purified by size exclusion chromatography (GE Healthcare, USA) using Superdex 200 in a 10 mM glycylglycine buffer solution at pH 5.5. N-terminal selectivity of the Fc region of the prepared FacVIIa-ATKAVC-PEG-Fc protein complex was examined by peptide mapping, and the selectivity was found to be 90% or higher.

Example 9: Preparation of Protein Complex Using PEG with Different Molecular Weight ALD-PEG-ALD (Nektar, USA), which is polyethylene glycol having a molecular weight of 10 kDa and aldehyde reactive groups at both ends thereof, was used to prepare and purify an insulin-10 kDa PEG conjugate in the same manner as in Example 5-2. The purified insulin-10 kDa PEG conjugate was concentrated to a concentration of about 5 mg/mL, and then used to prepare and purify an insulin-10 kDa PEG-Fc protein complex in the same manner as in Example 5-3.

Example 10: Preparation of Fab'-S-PEG-N-Fc Complex (—SH Group)

10-1. Expression and Purification of Fab'

An *E. coli* transformant BL21/poDLHF expressing anti-tumor necrosis factor-alpha Fab' (Accession No: KCCM 10511) was inoculated in 100 mL of LB medium and incubated under shaking overnight, and the culture broth was inoculated to a 5 L fermentor (Marubishi), followed by incubation at a temperature of 300 with aeration of 20 vvm at a stirring speed of 500 rpm. As fermentation proceeded, glucose and yeast extract were fed as an energy source required for cell growth according to the fermentation state of the microorganism. When absorbance OD value at 600 nm reached 80, IPTG was added to induce protein expression. Incubation was performed for about 40 hours to 45 hours to a high concentration, until absorbance OD value at 600 nm reached 120 to 140. The fermentation solution was centrifuged (20,000 g, 30 minutes) to discard a pellet and to collect only a supernatant.

The obtained supernatant was subjected to the following column chromatography to purify pure anti-tumor necrosis factor-alpha Fab'. The supernatant was added dropwise to a HiTrap protein G (Ge Healthcare, USA) column equilibrated with 20 mM phosphate buffer (pH 7.0), and elution was performed using 100 mM glycine (pH 3.0). The eluted Fab' fraction was added dropwise to a Superdex 200 (GE Healthcare, USA) column equilibrated with 10 mM sodium phosphate buffer (PBS, pH 7.3), and elution was performed using the same buffer. The eluted Fab' fraction was finally purified using a polyCAT 21×250 (PolyLC Inc. USA) column, and a pure anti-tumor necrosis factor-alpha Fab' fraction was eluted with a linear concentration gradient (sodium chloride concentration: 0.15 M→0.4 M) of 10 mM acetate buffer (pH 4.5).

10-2. Preparation and Purification of Fc-PEG Conjugate

Immunoglobulin Fc was dissolved in 100 mM sodium phosphate buffer (pH 5.5 to 6.5) at a concentration of 5 mg/mL, and NHS-PEG-MAL was removed therefrom. The buffer was exchanged, and then the reactant was applied to a polyCAT (PolyLC Inc. USA) column, and an immunoglobulin Fc-PEG conjugate was first eluted with a linear concentration gradient (sodium chloride concentration: 0.15 M→0.5 M) of 20 mM sodium phosphate buffer (pH 6.0), and then unreacted immunoglobulin Fc was eluted and removed.

10-3. Preparation and Purification of Fab'-S-PEG-N-Fc Complex (—SH Qroup)

Fab' purified in Example 10-1 was dissolved in 100 mM sodium phosphate buffer at a concentration of 2 mg/mL, and then the immunoglobulin Fc-PEG conjugate prepared in Example 10-2 was added to the same buffer at a molar ratio of Fab':conjugate of 1:5. The solution was concentrated to a final protein concentration of 50 mg/mL, and reaction was allowed at 4° C. to 8° C. under slow stirring for about 24 hours.

After completion of the coupling reaction, the reaction solution was added dropwise to a Superdex 200 (GE Healthcare, USA) column equilibrated with 10 mM sodium phosphate buffer (pH 7.3), and elution was performed by applying the same buffer at a flow rate of 1 mL/min. The Fab'-S-PEG-N-Fc complex was first eluted due to its high molecular weight, and then unreacted immunoglobulin Fc-PEG conjugate and Fab' were eluted and removed.

To completely remove the unreacted immunoglobulin Fc, the eluted Fab'-S-PEG-N-Fc complex fraction was added dropwise to a polyCAT 21×250 (PolyLC Inc. USA) column, and the pure Fab'-S-PEG-N-Fc complex (Fc-PEG conjugate linked to —SH group at the C-terminus of Fab') was eluted with a linear concentration gradient (sodium chloride concentration: 0.15 M→0.5 M) of 20 mM sodium phosphate buffer (pH 6.0).

Example 11: Preparation of Fab'-N-PEG-N-Fc Complex (N-Terminus)

11-1. Preparation and Purification of Fab'-PEG Conjugate (N-Terminus)

40 mg of purified Fab' obtained in Example 10-1 was dissolved in 100 mM sodium phosphate buffer (pH 5.5 to 6.5) at a concentration of 5 mg/mL, and then ButylALD-PEG-ButylALD (molecular weight 3.4 kDa, Nektar Inc., USA) was added at a molar ratio of Fab':PEG of 1:5. A reducing agent, sodium cyanoborohydride (NaCNBH$_3$, Sigma), was added at a final concentration of 20 mM, and reaction was allowed at 4° C. to 8° C. under slow stirring for about 2 hours.

After completion of the reaction, the reaction buffer was exchanged with 20 mM sodium phosphate buffer (pH 6.0). After exchanging the buffer, the reactant was applied to a polyCAT (PolyLC Inc. USA) column, and a Fab'-PEG conjugate fraction was first eluted with a linear concentration gradient (sodium chloride concentration: 0.15 M→0.4 M) of 20 mM acetate buffer (pH 4.5), and then unreacted Fab' was eluted and removed.

11-2. Preparation and Purification of Fab'-N-PEG-N-Fc Complex

The Fab'-PEG conjugate purified in Example 11-1 was dissolved in 100 mM sodium phosphate buffer (pH 6.0) at a concentration of 10 mg/mL, and then the immunoglobulin Fc dissolved in the same buffer was added at a molar ratio of Fab'-PEG conjugate:Fc of 1:5. The solution was concentrated to a final protein concentration of 50 mg/mL. A reducing agent, sodium cyanoborohydride (NaCNBH$_3$, Sigma), was added at a final concentration of 20 mM, and reaction was allowed at 4° C. to 8° C. under slow stirring for about 24 hours.

After completion of the coupling reaction, the reaction solution was added dropwise to a Superdex 200 (GE Healthcare, USA) column equilibrated with 10 mM sodium phosphate buffer (pH 7.3), and elution was performed by applying the same buffer at a flow rate of 1 mL/min. The coupled Fab'-N-PEG-N-Fc complex was first eluted due to its high molecular weight, and then unreacted immunoglobulin Fc and Fab'-PEG conjugate were eluted and removed. To completely remove the unreacted immunoglobulin Fc, the eluted Fab'-N-PEG-N-Fc complex fraction was further applied to a polyCAT 21×250 (PolyLC Inc. USA) column, and the pure Fab'-N-PEG-N-Fc complex (immunoglobulin Fc-PEG conjugate linked to the N-terminus of Fab') was eluted with a linear concentration gradient (sodium chloride concentration: 0.15 M→0.5 M) of 20 mM sodium phosphate buffer (pH 6.0).

The protein complexes prepared in Examples were analyzed by the following Experimental Examples.

Experimental Example 1: Evaluation of Purity of Protein Complex 1-1. Identification of Protein Complex The protein complexes prepared in the above Examples were analyzed by non-reduced SDS-PAGE using a 4% to 20% gradient gel and a 12% gel. SDS-PAGE analysis and Western blot analysis of individual protein complexes using antibodies against immunoglobulin Fc and physiologically active polypeptides were performed. As shown in FIG. 1, a coupling reaction resulted in the successful production of IFNα-PEG-Fc (A), hGH-PEG-Fc (B), $^{17,65}$S-G-CSF-PEG-Fc (C), Insulin-PEG-Fc (D), EPO-PEG-Fc (E), CA-Exendin4-PEG-Fc (F), and FacVII-PEG-Fc (G).

1-2. Evaluation of Purity of Protein Complex

The protein complexes prepared in the above Examples, IFNα-PEG-Fc (A), hGH-PEG-Fc (B), $^{17,65}$S-G-CSF-PEG-Fc (C), Insulin-PEG-Fc (D), EPO-PEG-Fc (E), and CA-Exendin4-PEG-Fc (F), were subjected to size exclusion chromatography, reverse phase chromatography, or ion exchange chromatography using HPLC, respectively. As shown in FIG. 2, they displayed a single peak corresponding to high purity of 95% or higher in each analysis.

1-3. Examination of Site Selectivity of Protein Complex

The protein complexes prepared in Examples, IFNα-PEG-Fc (A), hGH-PEG-Fc (B), $^{17,65}$S-G-CSF-PEG-Fc (C), insulin-PEG-Fc (D), and EPO-PEG-Fc (E), were subjected to peptide mapping analysis (reverse phase chromatography) using protease, respectively. As shown in FIG. 3, it was confirmed that the protein complexes linked via the N-terminus of the immunoglobulin Fc region with high selectivity of 90% or higher were prepared.

Experimental Example 2: Comparison of Efficacy of Complex Depending on Fc Binding Position The protein complexes prepared in Examples, CA-Exendin4-PEG-Fc, $^{17,65}$S-G-CSF-PEG-Fc, and EPO-PEG-Fc, were subjected to in vitro and in vivo efficacy tests, respectively. As shown in the following Table, binding to the N-terminus (proline) of Fc showed better efficacy than binding to other regions (e.g., lysine).

TABLE 1

| in vitro activity - CHO/GLP-1R bioassay of CA Exendin-PEG-Fc positional isomers | | |
|---|---|---|
| Test material | EC$_{50}$ (ng/mL) | % vs. Experimental group |
| CA Exendin (lysine)-PEG-(N-terminus) Fc-Experimental group | 95.35 | 100.00 |
| CA Exendin (lysine)-PEG-(lysine) Fc | 590.57 | 16.15 |

As shown in Table 1, comparison of in vitro activities between CA Exendin-PEG-Fc positional isomers showed that the CA Exendin-PEG-Fc complex of the present invention, which was prepared by specific binding to N-terminus of immunoglobulin Fc fragment, has 6 times higher potency than a CA Exendin-PEG-Fc complex which was prepared by binding to another position of an immunoglobulin Fc region.

TABLE 2

| in vitro activity - mouse bone marrow cell proliferation assay of $^{17,65}$S-G-CSF-PEG-Fc positional isomers | | |
|---|---|---|
| Test material | EC$_{50}$ (ng/mL) | % vs. Experimental group |
| $^{17,65}$S-G-CSF (N-terminus)-PEG-(N-terminus) Fc-Experimental group | 134.43 | 100.00 |
| $^{17,65}$S-G-CSF (N-terminus)-PEG-(lysine) Fc | 225.87 | 59.50 |

As shown in Table 2, comparison of in vitro activities between $^{17,65}$S-G-CSF-PEG-Fc positional isomers showed that the $^{17,65}$S-G-CSF-PEG-Fc complex of the present invention, which was prepared by specific binding to a N-terminus of immunoglobulin Fc fragment, has about 67% increased titer, compared to a $^{17,65}$S-G-CSF-PEG-Fc complex which was prepared by binding to another position of an immunoglobulin Fc region.

Meanwhile, to examine in vivo activities of the protein complex of the present invention, in particular, EPO-PEG-Fc positional isomers, a normocythemic mice assay was performed to measure reticulocyte levels after subcutaneous injection of EPO-PEG-Fc into normocythemic mice.

TABLE 3

Measurement of in vivo bio-potency - reticulocyte level of EPO-PEG-Fc positional isomers (after subcutaneous injection into normocythemic mice)

| Test material | Bio-potency (IU/mg) | % vs. Experimental group |
|---|---|---|
| EPO (N-terminus 84.4%)-PEG-(N-terminus 100%) Fc-Experimental group | 14,189,403 | 100.00 |
| EPO (N-terminus 38.2%)-PEG-(lysine 83.0%) Fc | 9,951,501 | 70.10 |

As shown in Table 3, comparison of in vivo activities between EPO-PEG-Fc positional isomers showed that the EPO-PEG-Fc complex of the present invention, which was prepared by specific binding to N-terminus of immunoglobulin Fc fragment, has about 40% increased titer, compared to an EPO-PEG-Fc complex which was prepared by binding to another position of an immunoglobulin Fc region.

These results suggest that when the protein complex comprising the physiologically active polypeptide, the non-peptidyl polymer, and the immunoglobulin Fc region is prepared by using a specific site of the immunoglobulin Fc fragment as a binding site, the protein complex shows an improved in vivo activity of the physiologically active polypeptide.

With the Examples and Experimental Examples taken together, the present inventors prepared the protein complex comprising the physiologically active polypeptide, the non-peptidyl polymer, and the immunoglobulin Fc region in order to increase in vivo duration of the physiologically active polypeptide and to increase or maintain in vivo activity (potency) at the same time. In detail, protein complexes were prepared using various physiologically active polypeptides, and in particular, protein complexes were prepared by using a specific site, that is, the N-terminus of an immunoglobulin Fc region, as a binding site.

As a result, it was confirmed that various protein complexes prepared by the preparation method of the present invention showed more than 90% N-terminal selectivity of an immunoglobulin Fc region, and the protein complexes of the present invention, which were prepared by specific binding to a N-terminus of an immunoglobulin Fc fragment, have about 40% to 400% increased titer, compared to protein complexes which were prepared by binding to another position of an Fc region.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds, are therefore intended to be embraced by the claims.

The invention claimed is:

1. A protein complex comprising a physiologically active polypeptide linked to an immunoglobulin Fc region via a non-peptidyl polymer having two functional ends, wherein the non-peptidyl polymer is site-specifically linked to a N-terminus of the immunoglobulin Fc region,
wherein the physiologically active polypeptide is a granulocyte colony-stimulating factor derivative in which the amino acids at positions 17 and 65 of the native G-CSF is substituted with serine,
wherein the immunoglobulin Fc region comprises the sequence of SEQ ID NO: 1, and
wherein the non-peptidyl polymer is polyethylene glycol.

2. The protein complex of claim 1, wherein both of the two functional ends of the non-peptidyl polymer is respectively linked to the physiologically active polypeptide and the immunoglobulin Fc region through a reactive group by a covalent bond.

3. The protein complex of claim 1, wherein the immunoglobulin Fc region is aglycosylated.

4. The protein complex of claim 2, wherein the reactive group of the non-peptidyl polymer is selected from the group consisting of an aldehyde group, a maleimide group, and a succinimide group.

5. The protein complex of claim 4,
(a) wherein the aldehyde group is a propionaldehyde group or a butyraldehyde group; and
(b) wherein the succinimide group is succinimidyl carboxymethyl, succinimidyl valerate, succinimidyl methylbutanoate, succinimidyl methylpropionate, succinimidyl butanoate, succinimidyl propionate, N-hydroxysuccinimide, or succinimidyl carbonate.

6. The protein complex of claim 1,
(a) wherein the non-peptidyl polymer has an aldehyde group as the reactive group at both of the two functional ends;
(b) wherein the non-peptidyl polymer has an aldehyde group and a maleimide group as the reactive group at each of the two functional ends, respectively; or
(c) wherein the non-peptidyl polymer has an aldehyde group and a succinimide group as the reactive group at each of the two functional ends, respectively.

7. The protein complex of claim 1, wherein one of the two functional ends of the non-peptidyl polymer is linked to the N-terminus of the immunoglobulin Fc region and the other of the two functional ends of the non-peptidyl polymer is linked to a N-terminus, a C-terminus, or a free reactive group of a lysine residue, a histidine residue, or a cysteine residue of the physiologically active polypeptide.

8. A method of preparing the protein complex of claim 1, comprising:
(a) preparing a protein complex by linking at least one non-peptidyl polymer having a reactive group at both ends; at least one physiologically active polypeptide; and at least one immunoglobulin Fc region by a covalent bond; and
(b) isolating the protein complex, essentially comprising the covalently linked physiologically active polypeptide, non-peptidyl polymer, and immunoglobulin Fc region prepared in step (a), wherein the non-peptidyl polymer is linked to the N-terminus of the immunoglobulin Fc fragment,
wherein the physiologically active polypeptide is a granulocyte colony-stimulating factor derivative in which the amino acids at positions 17 and 65 of the native G-CSF is substituted with serine,
wherein the immunoglobulin Fc region comprises the sequence of SEQ ID NO: 1, and
wherein the non-peptidyl polymer is polyethylene glycol.

9. The method of claim 8, wherein step (a) comprises:
(a1) preparing a conjugate by linking one end of the non-peptidyl polymer to the immunoglobulin Fc region or the physiologically active polypeptide by a covalent bond; and
(a2) isolating the conjugate prepared in step (a1) and linking the other end of the non-peptidyl polymer of the isolated conjugate to the other of an immunoglobulin Fc region or the physiologically active polypeptide by a covalent bond.

10. The method of claim 9, wherein, in step (a1), the reaction mole ratio between the physiologically active polypeptide and the non-peptidyl polymer is in the range from 1:1 to 1:30, and the reaction mole ratio between the immunoglobulin Fc fragment and the non-peptidyl polymer is in the range from 1:1 to 1:20,
wherein step (a1) is performed in a pH condition from 4.0 to 9.0;
wherein step (a1) is performed at a temperature from 4.0° C. to 25° C.;
wherein, in step (a1), the reaction concentration of the immunoglobulin Fc region or physiologically active polypeptide is in the range from 0.1 mg/mL to 100 mg/mL;
wherein, in step (a2), the reaction mole ratio between the conjugate and the immunoglobulin Fc region or the physiologically active polypeptide is in the range from 1:0.1 to 1:20;
wherein step (a2) is performed in a pH condition from 4.0 to 9.0;

wherein step (a2) is performed at a temperature from 4.0° C. to 25° C.;
wherein, in step (a2), the concentration of the immunoglobulin Fc region or physiologically active polypeptide is in the range from 0.1 mg/mL to 100 mg/mL; or
wherein step (a1) and step (a2) are performed in the presence of a reducing agent.

11. The method of claim 10, wherein the reducing agent is selected from the group consisting of sodium cyanoborohydride (NaCNBH$_3$), sodium borohydride, dimethylamine borate, and pyridine borate.

12. The method of claim 9, wherein, in step (a2), the isolation is performed by a single or combined purification method selected from the group consisting of anion exchange chromatography, cation exchange chromatography, hydrophobic chromatography, affinity chromatography, and size exclusion chromatography.

13. The method of claim 12, wherein the functional group of the anion exchange chromatography resin is any one selected from the group consisting of quaternary ammonium (Q), quaternary aminoethyl (QAE), diethylaminoethyl (DEAE), polyethylene amine (PEI), dimethylaminomethyl (DMAE), and trimethylaminoethyl (TMAE);
wherein the functional group of the cation exchange chromatography resin is any one selected from the group consisting of methylsulfonate (S), sulfopropyl (SP), carboxymethyl (CM), sulfoethyl (SE), and polyaspartic acid;
wherein the functional group of the hydrophobic chromatography resin is any one selected from the group consisting of phenyl, octyl, (iso)propyl, butyl, and ethyl;
wherein the functional group of the affinity chromatography resin is any one selected from the group consisting of protein A, heparin, benzamidine, cobalt, nickel, copper and an antibody that binds to the protein complex or a part thereof, in which both ends of a non-peptidyl polymer are respectively conjugated to an immunoglobulin Fc region and a physiologically active polypeptide; or
wherein the resin of the size exclusion chromatography is selected from the group consisting of Superdex, Sephacryl, Superpose, and Sephadex.

14. The method of claim 8, wherein the isolation of the protein complex is performed by a single or combined method selected from the group consisting of anion exchange chromatography, cation exchange chromatography, hydrophobic chromatography, affinity chromatography, and size exclusion chromatography.

15. The method of claim 14, wherein the functional group of the anion exchange chromatography resin is any one selected from the group consisting of quaternary ammonium (Q), quaternary aminoethyl (QAE), diethylaminoethyl (DEAE), polyethylene amine (PEI), dimethylaminomethyl (DMAE), and trimethylaminoethyl (TMAE);
wherein the functional group of the cation exchange chromatography resin is any one selected from the group consisting of methylsulfonate (S), sulfopropyl (SP), carboxymethyl (CM), sulfoethyl (SE), and polyaspartic acid;
wherein the functional group of the hydrophobic chromatography resin is any one selected from the group consisting of phenyl, octyl, (iso)propyl, butyl, and ethyl;
wherein the functional group of the affinity chromatography resin is any one selected from the group consisting of protein A, heparin, benzamidine, cobalt, nickel, copper and an antibody that binds to the protein complex or a part thereof, in which both ends of a non-peptidyl polymer are respectively conjugated to an immunoglobulin Fc region and a physiologically active polypeptide; or
wherein the resin of the size exclusion chromatography is selected from the group consisting of Superdex, Sephacryl, Superpose, and Sephadex.

16. A method of preparing the protein complex of claim 1, comprising:
(a') preparing a conjugate by linking one end of a non-peptidyl polymer to an immunoglobulin Fc region or a physiologically active polypeptide by a covalent bond, which is performed in a pH condition from 4.0 to 9.0;
(b') isolating the conjugate prepared in step (a') and linking the other end of the non-peptidyl polymer of the isolated conjugate to the other of a immunoglobulin Fc region or the physiologically active polypeptide by a covalent bond, which is performed in a pH condition from 4.0 to 9.0; and
(c') isolating the protein complex, comprising the covalently linked physiologically active polypeptide, non-peptidyl polymer, and immunoglobulin Fc region prepared in step (b'), wherein the non-peptidyl polymer is linked to the N-terminus of the immunoglobulin Fc fragment,
wherein the physiologically active polypeptide is a granulocyte colony-stimulating factor derivative in which the amino acids at positions 17 and 65 of the native G-CSF is substituted with serine,
wherein the immunoglobulin Fc region comprises the sequence of SEQ ID NO: 1, and
wherein the non-peptidyl polymer is polyethylene glycol.

17. A method of preparing the protein complex of claim 1, comprising:
(a') preparing a conjugate by linking one end of a non-peptidyl polymer to an immunoglobulin Fc region or a physiologically active polypeptide by a covalent bond, wherein the reaction mole ratio between the physiologically active polypeptide and the non-peptidyl polymer is in the range from 1:1 to 1:30, and the reaction mole ratio between the immunoglobulin Fc region and the non-peptidyl polymer is in the range from 1:1 to 1:20, a reducing agent is contained in the range from 1 mM to 100 mM, the reaction is performed in the condition of pH from 4.0 to 9.0 at a temperature from 4.0° C. to 25° C., and the concentration of the immunoglobulin Fc region or physiologically active polypeptide is in the range from 0.1 mg/mL to 100 mg/mL;
(b') isolating the conjugate prepared in step (a') and linking the other end of the non-peptidyl polymer of the isolated conjugate to the other of a immunoglobulin Fc region or the physiologically active polypeptide by a covalent bond, wherein the reaction mole ratio between the conjugate and the immunoglobulin Fc region or the physiologically active polypeptide is in the range from 1:0.1 to 1:20, a reducing agent is contained in the range from 1 mM to 100 mM, the reaction is performed in the condition of pH from 4.0 to 9.0 at a temperature from 4.0° C. to 25° C., and the concentration of the immunoglobulin Fc region or physiologically active polypeptide is in the range from 0.1 mg/mL to 100 mg/mL; and
(c') isolating the protein complex, comprising the covalently linked physiologically active polypeptide, non-peptidyl polymer, and immunoglobulin Fc region prepared in step (b'), wherein the non-peptidyl polymer is linked to the N-terminus of the immunoglobulin Fc fragment, wherein the physiologically active polypeptide is a granulocyte colony-stimulating factor derivative in which the amino acids at positions 17 and 65 of the native G-CSF is substituted with serine, wherein the immunoglobulin Fc region comprises the sequence of SEQ ID NO: 1, and wherein the non-peptidyl polymer is polyethylene glycol.

18. A composition comprising the protein complex of claim 1 as an active ingredient.

19. The composition of claim 18, wherein the composition comprises the protein complex in an amount of 90% or higher.

20. A population comprising the protein complex of claim 1 in an amount of 90% or higher.

* * * * *

SEQUENCE LISTING

<160> NUMBER OF SEQ ID NOS: 1

<210> SEQ ID NO 1
<211> LENGTH: 221
<212> TYPE: PRT
<213> ORGANISM: Artificial Sequence
<220> FEATURE:
<223> OTHER INFORMATION: human immunoclobulin Fc region derivative monomer

<400> SEQUENCE: 1

```
Pro Ser Cys Pro Ala Pro Glu Phe Leu Gly Gly Pro Ser Val Phe Leu
1               5                   10                  15

Phe Pro Pro Lys Pro Lys Asp Thr Leu Met Ile Ser Arg Thr Pro Glu
                20                  25                  30

Val Thr Cys Val Val Val Asp Val Ser Gln Glu Asp Pro Glu Val Gln
            35                  40                  45

Phe Asn Trp Tyr Val Asp Gly Val Glu Val His Asn Ala Lys Thr Lys
        50                  55                  60

Pro Arg Glu Glu Gln Phe Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140
```

```
Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
                180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly Lys
        210                 215                 220
```